(12) United States Patent
Venter et al.

(10) Patent No.: US 11,618,029 B2
(45) Date of Patent: *Apr. 4, 2023

(54) DIGITAL TO BIOLOGICAL CONVERTER

(71) Applicant: Codex DNA, Inc., San Diego, CA (US)

(72) Inventors: J. Craig Venter, La Jolla, CA (US);
Daniel Gibson, Carlsbad, CA (US);
John E. Gill, San Marcos, CA (US)

(73) Assignee: Telesis Bio Inc., San Diego, CA (US)

( * ) Notice: Subject to any disclaimer, the term of this patent is extended or adjusted under 35 U.S.C. 154(b) by 181 days.

This patent is subject to a terminal disclaimer.

(21) Appl. No.: 17/321,301

(22) Filed: May 14, 2021

(65) Prior Publication Data

US 2021/0283615 A1 Sep. 16, 2021

Related U.S. Application Data

(63) Continuation of application No. 15/654,306, filed on Jul. 19, 2017, now Pat. No. 11,027,282, which is a
(Continued)

(51) Int. Cl.
*C12Q 1/68* (2018.01)
*B01L 7/00* (2006.01)
(Continued)

(52) U.S. Cl.
CPC ............. *B01L 7/52* (2013.01); *C07K 14/005* (2013.01); *C12N 7/00* (2013.01); *C12N 15/1089* (2013.01); *C12N 15/1093* (2013.01); *C12P 19/34* (2013.01)

(58) Field of Classification Search
CPC ....................................................... C12Q 1/68
(Continued)

(56) References Cited

U.S. PATENT DOCUMENTS 7,118,883 B2  10/2006  Noue et al.
7,164,992 B1   1/2007  Mulligan et al.
(Continued)

FOREIGN PATENT DOCUMENTS

JP   H08506813 A   7/1996
JP   2008-523786 A  7/2008
(Continued)

OTHER PUBLICATIONS

Alemdaroglu et al., "Generation of Multiblock Copolymers by PCR: Synthesis, Visualization and Nanomechanical Properties", Nano Letters, vol. 9, No. 10, Oct. 14, 2009, pp. 3658-3662.
(Continued)

*Primary Examiner* — Aaron A Priest
(74) *Attorney, Agent, or Firm* — DLA Piper LLP (US)

(57) ABSTRACT

The present invention provides a system for receiving biological sequence information and activating the synthesis of a biological entity. The system has a receiving unit for receiving a signal encoding biological sequence information transmitted from a transmitting unit. The transmitting unit can be present at a remote location from the receiving unit. The system also has an assembly unit connected to the receiving unit, and the assembly unit assembles the biological entity according to the biological sequence information. Thus, according to the present invention biological sequence information can be digitally transmitted to a remote location and the information converted into a biological entity, for example a protein useful as a vaccine, immediately upon being received by the receiving unit and without further human intervention after preparing the system for receipt of the information. The invention is useful, for example, for rapidly responding to viral and other biological threats that are specific to a particular locale.

23 Claims, 2 Drawing Sheets

Specification includes a Sequence Listing.

Related U.S. Application Data continuation of application No. 13/969,215, filed on Aug. 16, 2013, now Pat. No. 9,718,060.

(60) Provisional application No. 61/684,076, filed on Aug. 16, 2012.

(51) Int. Cl.
*C12N 15/10* (2006.01)
*C07K 14/005* (2006.01)
*C12N 7/00* (2006.01)
*C12P 19/34* (2006.01)

(58) Field of Classification Search
USPC .......................................................... 435/6.1
See application file for complete search history.

(56) References Cited

U.S. PATENT DOCUMENTS

| | | |
|---|---|---|
| 7,662,617 B2 | 2/2010 | Rush |
| 7,923,533 B2 | 4/2011 | Hyde et al. |
| 8,033,047 B2 | 10/2011 | Rasmussen et al. |
| 8,110,395 B2 | 2/2012 | Lewnard et al. |
| 2004/0223885 A1 | 11/2004 | Keen et al. |
| 2005/0267971 A1 | 12/2005 | Fritz |
| 2007/0269870 A1 | 11/2007 | Church et al. |
| 2010/0035768 A1 | 2/2010 | Gibson et al. |
| 2011/0124049 A1 | 5/2011 | Li |
| 2011/0207624 A1 | 8/2011 | Shen et al. |
| 2011/0250649 A1 | 10/2011 | Li et al. |
| 2012/0028843 A1 | 2/2012 | Ramu et al. |
| 2012/0052560 A1 | 3/2012 | Knight et al. |
| 2012/0220497 A1 | 8/2012 | Jacobson et al. |
| 2013/0296194 A1 | 11/2013 | Jacobson et al. |
| 2015/0031088 A1 | 1/2015 | Tian et al. |
| 2016/0144332 A1 | 5/2016 | Chu |

FOREIGN PATENT DOCUMENTS

| | | | | |
|---|---|---|---|---|
| WO | WO 1999/014318 A1 | 3/1999 | | |
| WO | WO 2004/070047 A1 | 8/2004 | | |
| WO | WO-2005059097 A2 * | 6/2005 | .............. | C12P 19/34 |
| WO | WO 2006/044596 A1 | 4/2006 | | |
| WO | WO 2006/076679 A1 | 7/2006 | | |
| WO | WO-2008024319 A2 * | 2/2008 | .......... | B01J 19/0046 |
| WO | WO 2008/028024 A2 | 3/2008 | | |

OTHER PUBLICATIONS

De Rocquigny et al., First Large Scale Chemical Synthesis of the 72 Amino Acid HIV-1 Nucleocapsid Protein NCp7 in an Active Form; Biochemical and Biophysical Research Communications. Oct. 31, 1991, vol. 180, No. 2, pp. 1010-1018.

Densmore et al., "Algorithms for automated Dna assembly", Nucleic Acids Research vol. 38, No. 8, 2607-2616.

Ellis et al., "DNA assembly for synthetic biology: from parts to pathways and beyond"; Integrative Biology, vol. 3, No. 2, Jan. 1, 2011, p. 109, XP055047340.

European Examination Report dated Dec. 13, 2016, regarding EP 13 829 140.6.

European Examination Report dated Jul. 2, 2019, regarding EP 13 829 140.6.

European Examination Report dated May 28, 2018, regarding EP 13 829 140.6.

Extended European Search Report dated Apr. 7, 2016, regarding EP 13 8291 40.6.

Geallai et al., "Nonviral delivery of self-amplifying RNA vaccines"; PNAS, Jul. 26, 2012, 6 pgs.

Gibson et al., "Enzymatic assembly of DNA molecules up to several hundred kilobases"; Nature Methods, vol. 6, No. 5, Apr. 12, 2009. pp. 343-345.

Gibson et al., Creation of a Bacterial Cell Controlled by a Chemically Synthesized Genome; Science, vol. 329, No. 5987, Jul. 2, 2010, pp. 52-56, XP055082599.

Gibson et al., "Chemical synthesis of the mouse mitochondria) genome"; Nature Methods, vol. 7, No. 11, Nov. 1, 2010, pp. 901-903. XP055173787.

Hekele et al., "Rapidly produced SAM® vaccine against H7N9 influenza is Immunogenic in mice"; Emerging Microbes and Infections, (2013) 2, e52, 7pgs.

Hillson et al., "j5 DNA Assembly Design Automation Software"; ACS synthetic biology, vol. 1, No. 1, Jan. 20, 2012, pp. 14-21, XP055325880.

Huang et al., "Integrated two-step gene synthesis in a microfluidic device", Lab on a Chip 9(2):276-85, Mar. 2009.

International Search Report Re PCT/US2013/055454.

Japanese Office Action dated Apr. 26, 2018, regarding JP 2015-527674.

Japanese Office Action dated Jun. 21, 2017, regarding JP 2015-527674.

Li et al., "Impedance Sensing of DNA Binding Drugs Using Gold Substrates Modified with Gold Nanoparticles"; Anal. Chem. 2005, 77:478-485.

Ma et al., "DNA synthesis, assembly and applications in synthetic biology", Current Opinion in Chemical Biology, vol. 16, No. 3-4, Aug. 1, 2012, pp. 260-267.

Ma et al., "Error correction in gene synthesis technology", Trends Biotechnol. Mar. 2012;30(3):147-54.

New England Biolab product data sheet M0206S sold since 2012.

Notka et al., "Industrial scale gene synthesis"; Methods in Enzymology, Academ. Press, USA, vol. 498, Jan. 1, 2011, pp. 247-275, XP009192694.

Quan et al., "Parallel on-chip gene synthesis and application to optimization of protein expression", Nat Biotechnol. May 2011;29(5):449-52.

Xiong et al., "Chemical gene synthesis: strategies, softwares, error corrections, and applications", FEMS Microbiol Rev. May 2008;32 (3):522-40.

\* cited by examiner

DIGITAL TO BIOLOGICAL CONVERTER

CROSS-REFERENCE TO RELATED APPLICATIONS

This application is a continuation application of U.S. application Ser. No. 15/654,306 filed Jul. 19, 2017, now pending, which is a continuation application of U.S. application Ser. No. 13/969,215 filed Aug. 16, 2013, now issued as U.S. Pat. No. 9,718,060; which claims the benefit under 35 USC § 119(e) to U.S. Application Ser. No. 61/684,076 filed Aug. 16, 2012. This disclosure of each of the prior applications is considered part of and is incorporated by reference in the disclosure of this application.

INCORPORATION BY REFERENCE OF SEQUENCE LISTING

The material in the accompanying Sequence Listing is hereby incorporated by reference into this application. The accompanying sequence listing text file, named CODEX1600-3_ST25, was created on May 14, 2021 and is 15 kB in size. The file can be accessed using Microsoft Word on a computer that uses Windows OS.

BACKGROUND OF THE INVENTION

Field of the Invention

The invention pertains to the automated conversion of biological information, such as a biological sequence of interest, into a final biological entity. The invention also pertains to providing for, e.g., a rapid response to biological threats.

Background Information

The following description of the background of the invention is provided to aid in understanding the invention, but is not admitted to be nor to describe, prior art to the invention.

Genetic information is stored in the form of a sequence of nucleotides that form a DNA molecule, which thus encodes the information necessary for the biological synthesis of proteins and peptides necessary for all cellular processes. Digital technology allows the transmission of digital information across enormous distances within seconds. This information is useful for any number of processes that convert the digital information into a useful function. It would be very desirable to have a system that allows the transmission of biological information in digital form across great distances, and then the conversion of that digital information into any of a wide variety of biological entities. Such biological entities would then be useful for the performance of a wide variety of biological functions such as, for example, the response to a biological threat to a community. A desirable system would also allow for the use of the biological information for the synthesis of DNA molecules, RNA molecules, proteins, virus and phage particles, vaccines, and synthetic cells.

With respect to responding to a biological threat, one important aspect can be the provision of a sufficient quantity of vaccine to inoculate a sufficient number of the members of the population against the threat. A critical item of information necessary to manufacture a vaccine is the biological sequence information associated with the biological threat. When the biological threat is a virus, that sequence information can be obtained by deriving the sequence information from a viral sample. Once the sequence is determined, a vaccine can be manufactured. This can take a variety of formats, one of which is to manufacture the protein coat or portion thereof of the viral threat, or another antigenic component of the biological threat, which will provide the antigen to stimulate a response in inoculated individuals against the biological threat.

Thus, for example, a nucleic acid sequence coding for the antigen can be synthesized. This can involve up to several days of work to coordinate the synthesis of oligonucleotides, which can then be assembled to form the final nucleic acid sequence. This can also involve the participation of several laboratories. After being obtained the final nucleic acid sequence can then be translated, whether in vitro or in vivo, to synthesize the antigenic protein.

In the response to a biological threat, time can be of the utmost importance, so that members of medical response teams who will implement a response plan or work directly with infected persons can be inoculated and thus obtain immunity from the threat and be available to continue to carry out their duties unimpeded by threats of illness. Delays in vaccine preparation also lead to insufficient quantities of vaccine being ready at critical times and are also an important limiting factor in responding to a biological threat.

Furthermore, the specifics of a viral or other biological threat often differ from one locale to another. Thus, a vaccine that might be maximally effective in one locale may not be as effective in another locale due to rapid virus mutation.

There is therefore a need for systems that can transmit biological information in digital form, and allow for the conversion of that digital information into a variety of biological final products. Having a system that is automated would also contribute greatly to achievement of these goals. Such a system will meet various biological challenges, such as rapidly and effectively responding to viral and other biological threats for which time may be critical. It would also allow for a response that is tailored from one locale to another to meet the specific threats present in various locales.

SUMMARY OF THE INVENTION

The present invention provides systems and methods for receiving biological sequence information from a remote location and the automated synthesis of a biological entity based on the biological sequence information. The system and methods enable a rapid response to viral and other biological threats that are specific to a particular locale. Kits are also provided that include materials and reagents for performing the methods on systems of the invention. The system is able to produce a biological entity such as a DNA molecule, an RNA molecule, protein, or peptide from the biological sequence information in an automated fashion, and is further able to produce viral particles in vivo, also in automated fashion. The system is thus useful in the production of vaccines, such as an influenza vaccine.

In a first aspect the invention provides a system for receiving biological sequence information and activating the synthesis of a functional biological entity. The system has a receiving unit for receiving a signal encoding biological sequence information transmitted from a transmitting unit, the transmitting unit present at a remote location from the receiving unit. The system also has an assembly unit connected to the receiving unit, for assembling the biological entity according to the biological sequence information. The assembly unit has or is connected to reagent vessels containing biological building block molecules and/or already synthesized oligonucleotides, and also has components for transporting reagents within the system and for executing steps in an automated method for synthesizing the functional biological entity. The receiving unit of the system receives the biological sequence information and provides it to the assembly unit.

In one embodiment transmitting unit and the receiving unit are computers that are part of a computer network. The biological building block molecules can be dNTPs or nucleoside phosphoramidites. The system can also have programming instructions for assembling the dNTPs or nucleoside phosphoramidites into a set of oligonucleotides according to the biological sequence information. It can also have programming instructions for assembling the set of oligonucleotides into a DNA molecule. In one embodiment the functional biological entity is a DNA molecule. The oligonucleotides can also be provided to the system or methods of the invention already synthesized and the system or method is for assembling the oligonucleotides into a DNA molecule.

The system in one embodiment has one or more vessels containing reagents for the transcription and/or translation of the functional DNA molecule into a biological product. The biological sequence information can encode a nucleic acid encoding for at least a portion of a virus particle or bacteriophage. The assembly unit can also convert the biological entity into a biological product, and in some embodiments the biological product can be a virus particle or a portion of a virus particle or a phage or cells. The virus particle or portion of a virus particle can be a protein antigen. In some embodiments the assembly unit also has, or is connected, one or more vessels containing a host cell. The systems of the invention can also have one or more vessels and reagents for the transcription of the DNA molecule into an RNA molecule, and/or for the translation of an RNA molecule into a functional peptide or protein, which translation can be done in vitro or in vivo. The system can also have programming instructions for performing steps of an automated method in distinct reaction zones of a reaction container.

In another aspect the invention provides methods of synthesizing a functional biological entity. The method involves receiving biological sequence information from a transmitting unit in a system for synthesizing the functional biological entity. The system of the methods is a system of the invention described herein. The method further involves synthesizing the functional biological entity in an automated method.

In the methods the assembly unit can be prepared for assembly of the functional biological entity prior to receiving the biological sequence information. The preparation can involve charging reaction containers of the system with biological building blocks or building block polymers, such as dNTPs or nucleoside phosphoramidites or with already synthesized oligonucleotides or peptides. In some methods of the invention the biological sequence information encodes for a nucleic acid molecule encoding for at least a portion of a virus particle. In methods where a functional protein or peptide is produced, it can be a viral protein or peptide. The functional biological entity can also be a DNA molecule larger than 5 kb.

In one embodiment of the methods the building block molecules are linked in an in vitro reaction to form building block polymers. The building block molecules can be nucleotides or nucleoside phosphoramidites, and the building block polymers can be oligonucleotides or peptides or ribonucleotides or derivatives of any.

In some embodiments the methods involve transporting oligonucleotides from a first zone of a reaction container to a second zone of the reaction container. The methods can also involve performing one step of the method in a first reaction zone of the reaction container and a second step of the method in a second reaction zone of the reaction container. In one embodiment the first step is the assembly of a DNA molecule and the second step is the transcription of the DNA molecule into an RNA. The methods can also have a third step performed in a third reaction zone of the reaction container, the third step comprising the in vivo production of viral particles. In other embodiments synthesizing the biological entity comprises a DNA assembly step. The steps of the method can also involve multiple levels of biological assembly. Thus the methods can have a DNA assembly step and a RNA transcription step. The DNA assembly step can be performed in a first reaction zone of the reaction container and the RNA transcription step can be performed in a second reaction zone of the reaction container. The method can also have a step involving the in vivo production of viral particles in a third reaction zone of the reaction container.

The summary of the invention described above is not limiting and other features and advantages of the invention will be apparent from the following detailed description of the invention, and from the claims.

BRIEF DESCRIPTION OF THE DRAWINGS

FIG. 2A Lane 1: A/Brisbane/10/2010(H1N1)_HA; Lane 2: A/Brisbane/10/2010(H1N1)_NA; Lane 3: X179A TD(H1N1)_HA; Lane 4: X179A(H1N1)_NA; Lane 5: A/Victoria/361/2011_CDC/E3(H3N2)_HA; Lane 6: A/Victoria/361/2011(H3N2)_NA; Lane 7: A/Brisbane/256/2011_P2/E3(H3N2)_HA; Lane 8: A/Brisbane/256/2011_P2/E3(H3N2)_NA; Standards lane. FIG. 2B Standards lane; Lane 1: B/Texas/06/2011_BX-45 HA; Lane 2: B/Texas/06/2011_BX-49 NA; Lane 3: B/New Hampshire/1/2012_HA; Lane 4: B/New Hampshire/1/2012_NA; Lane 5: B/Brisbane/60/08_HA; Lane 6: B/Brisbane/60/08_NA; Lane 7: B/Nevada/03/2011_v2_HA; Lane 8: B/Nevada/03/2011_v2_NA.

DETAILED DESCRIPTION OF THE INVENTION

The present invention provides a system for the transmission of biological information in digital form across great distances, and the subsequent and rapid conversion of that information into a final biological entity. The biological sequence information can be that information necessary for the synthesis of a DNA molecule, an RNA molecule, a protein or peptide, virus and/or phage particles, vaccines, synthetic cells, or any biological entity. The biological entities can be synthesized by a system of the invention located at the particular locale where the biological entity is to be assembled or synthesized.

The invention provides numerous advantages with respect to rapidly responding to biological threats. In one embodiment the biological threat is a viral threat. The invention allows for biological sequence information to be rapidly transmitted to a location under a biological threat, for example a remote location, and immediately be used in the process for preparing the vaccine or other materials necessary for an appropriate response. The threat can be an influenza or other viral threat.

In one embodiment the biological sequence information is the sequence information necessary for the formulation of a vaccine to the virus, i.e., the sequence of one or more varying regions of the virus particle. The invention therefore allows for a system of the invention to be set up and prepared with necessary reagents ahead of time so that the system can receive biological sequence information and immediately and in an automated manner begin preparing a vaccine or other appropriate biological response to deal with the threat immediately upon receiving the sequence information. The community under threat can therefore have multiple or large-scale systems prepared to receive the sequence information in order to maximize the supply of vaccine that will be available within a short timeframe for inoculating a population against the biological threat. The invention is versatile and allows a vaccine to be customized for dealing with the specific viral threat in a particular locale. Thus, where different strains of virus are affecting different locales, each locale can tailor a vaccine response to the particular strain affecting that locale in order to respond most accurately and effectively to the threat. By reducing or eliminating the number of hours that pass prior to beginning preparation of the vaccine and by preparing the most effective vaccine for the subject locale, the effectiveness of the response to the biological threat is greatly improved.

The present invention also has applicability to responding to biological threats related to bioterrorism where the rapidity and accuracy of the response may impart a critical and lifesaving effectiveness to the response. Thus, locales facing such threats can prepare by setting up a system disclosed herein in order to be able to mount the fastest and most accurate response, and thus have the greatest chance of defeating the threat with minimal damage.

The systems of the invention can be designed so that the methods can be performed on any reaction containers containing a plurality of reaction areas where samples can be manipulated. The reaction areas can be either defined (i.e., by physical boundaries on the container) or undefined (i.e., defined only by the space occupied by a sample). In one embodiment the reaction container is a standard 96-well plate, which contains a plurality of small reaction areas accommodating samples to be manipulated, i.e., each well of the plate. This is convenient because thermocyclers used in the systems and methods of the invention are typically designed to hold a 96 well plate. But it will be realized that any type of reaction container that holds a plurality of reaction areas containing samples to be manipulated will also function in the invention. For example a reaction plate having other than 96 wells will be a suitable reaction container in the methods, or a petri dish having a plurality of reaction areas where sample can be manipulated is also suitable even if the reaction areas are not defined by physical boundaries. Even a biochip can be a reaction container since it has a plurality of reaction areas on the chip.

By defining and utilizing reaction zones on the reaction containers it was discovered that a system can be designed so that a multi-level process from synthesizing oligonucleotides to the production of a protein or vaccine and additional methods can be performed in an automated method. This is accomplished by performing particular steps in reaction areas located in a specific reaction zone on the reaction container.

By employing robotics in the invention samples can be transported from particular reaction zones of a reaction container to other reaction zones, and an automated method can be conducted in one reaction container. Samples are not harmed or destroyed by conditions (e.g., temperature) for carrying out subsequent steps in a process in the same reaction container because the appropriate conditions for subsequent steps can be established on the reaction container prior to the system moving the sample into the reaction zone where the next step will occur. Thus, the reaction samples can be moved across the reaction container and into a new zone as each subsequent step is performed and the conditions created on the reaction container for that subsequent step, and the entire process can be completed in an automated method in the same reaction container. Thus, in some embodiments the systems of the invention perform automated methods.

An automated method is one where no human intervention is necessary after the method is initiated—the method goes to completion from that point without a human having to perform any action, and the method produces a functional biological entity. For example, in one embodiment an automated method is a method where no human intervention occurs after sequence instructions are received by the system of the invention, and the system executes the method to produce a functional nucleic acid molecule. Human intervention is any action taken by a person to move the method to completion. Human intervention includes, but is not limited to, the manual movement of samples or of the reaction container from one location to another or an action involving the preparation or movement of samples or reagents, the provision or re-supply of reagents or reactants, the turning on or off of any component of the system, or any other action necessary to complete execution of the method. In one example of an automated method is initiated with the receipt of biological sequence information from a transmitting unit. The method can proceed as an automated method to result in production of a DNA molecule, and in one embodiment has multiple levels of biological assembly and proceeds to the transcription of the DNA to produce mRNA, and can also proceed further to the translation of the mRNA into a protein biological product.

The system of the invention can have multiple levels of biological assembly so that a synthesized DNA molecule, for example, can be transcribed into an RNA molecule, and the RNA molecule further translated into a protein or peptide of interest, or combined with a cell culture to result in production of a drug product or synthesis of a whole vaccine. Translated proteins can also be further processed by the system to produce, for example, a viral particle or vaccine, or portions thereof. Levels of assembly include 1) synthesis of a dsDNA or ssDNA molecule from linking nucleotides or nucleoside phosphoramidites; 2) assembly of a dsDNA molecule by joining oligonucleotides (a DNA assembly step); 3) synthesis/transcription of an RNA molecule according to a DNA molecule (a transcription step); 4) synthesis of a protein or peptide from joining amino acids or synthesis of a protein from joining peptides; 5) synthesis/translation of a protein or peptide according to the sequence of an RNA molecule (a translation step); 6) assembly of two or more proteins (or protein sub-units) into a protein having quartenary structure (e.g., a virus particle or portion thereof). The systems and methods of the invention can perform any of these levels of assembly. A system or method that performs at least two of these levels of synthesis is a system or method having multiple levels of biological assembly, but systems and methods can also be devised having at least 3 levels or at least 4 levels or at least 5 levels of biological assembly. In one embodiment the systems and methods of the invention synthesize a dsDNA molecule from nucleotides (including derivatives) or nucleoside phosphoramidites (including derivatives). In another embodiment the systems and methods of the invention synthesize a ssDNA or dsDNA molecule from oligonucleotides. In another embodiment the systems and methods of the invention synthesize a protein or peptide from amino acids. The oligonucleotides or peptides of the invention can also be modified, derivatized, or labeled, as described herein.

Figure 1:
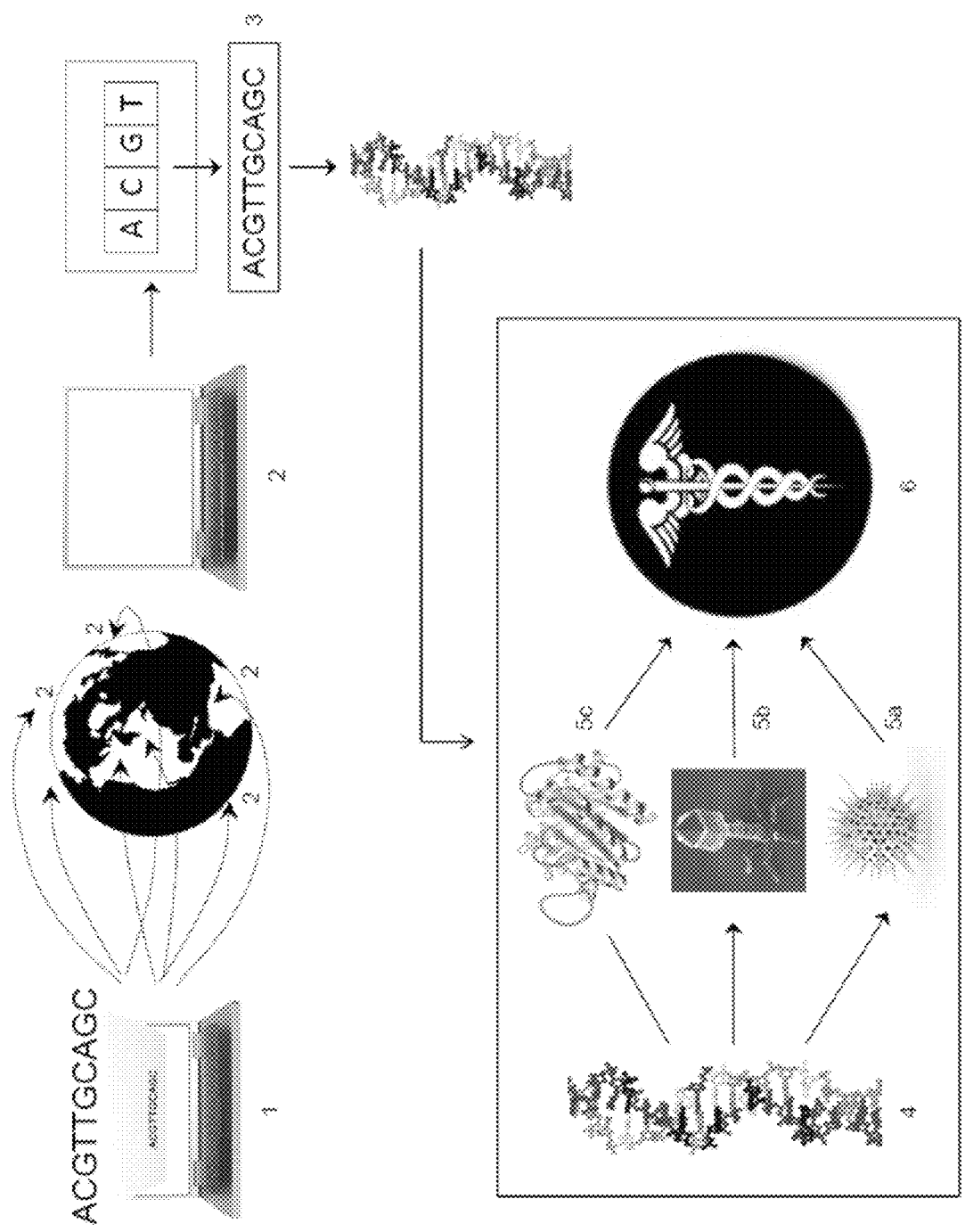
FIG. 1 provides a graphical illustration of a use of the present invention, broadly depicting the transmission of biological information and its conversion into a useful biological entity.

With reference to FIG. 1 there is depicted an embodiment of the invention. A transmitting unit 1 transmits biological sequence information 3 from a location to the receiving units 2 of various systems of the invention located in locations remote from the transmitting unit 1. The receiving units 2 receive the signal encoding biological sequence information 3 and provide the biological sequence information to an assembly unit. The assembly unit assembles the biological entity 4, which in this embodiment is a DNA molecule. In this embodiment the assembly unit further converts the biological entity into a biological product 5, which can be a virus coat or portion thereof 5*a*, or a virus 5*b*, or a protein antigen 5*c*. The biological product is useful as a vaccine 6.

Receiving Unit

The receiving unit receives a signal encoding biological sequence information. In one embodiment the receiving unit is a computer that receives digitally encoded biological sequence information from the transmitting unit. The receiving unit can therefore be connected to the internet and/or can be otherwise connected to a computer network, which allows information to be exchanged between computers connected to the network. The internet is also a computer network as the term is used herein. In one embodiment the transmitting unit is located in a location remote from the receiving unit, for example in another city or another country or nation. The receiving unit can even be located in a place off of the Earth or outside of the Earth's atmosphere such as, for example, in an orbiting space station or even on the Moon or on a planet other than Earth. In some embodiments the transmitting unit is located in a remote location that is at least 10 miles or at least 25 miles or at least 50 miles or at least 100 miles or at least 250 miles or at least 1000 miles from the receiving unit. In some embodiments the receiving unit receives the biological sequence information and provides it to the assembly unit in a form that the assembly unit can convert into programming instructions for the assembly of the biological sequence. The receiving unit in one embodiment is therefore connected to the transmitting unit through a computer network. The receiving unit is also connected to the assembly unit. In various embodiments the receiving unit can also be a computer or circuit board or part of a computer integrated into the assembly unit, or a sub-unit of the assembly unit. The connections between the receiving unit and transmitting unit can be indirect, i.e., through one or more additional computers, routers, or other electronic devices interposed between them. The connection can also be through a wireless or satellite connection. The connection can also be direct, as in a direct connection between the transmitting unit and receiving unit through the computer network. However, the receiving unit will receive the signal transmitted by the transmitting unit. In one embodiment the receiving unit receives the biological sequence in the form of electromagnetic waves and provides the sequence to the assembly unit for assembly of the biological entity or biological product.

Transmitting Unit

The transmitting unit transmits biological sequence information to the receiving unit of the system. A digital signal can represent information in the form of a series of binary digits. Persons of ordinary skill in the art understand that virtually any kind of information can be readily transmitted as a digital signal, including biological sequence information. These types of information are readily transmitted through computer networks, which can span the globe. In one embodiment of the invention the transmitting unit is a computer that is connected to a computer network that allows information to be transmitted from one computer to another, or exchanged between computers connected to the network (e.g., the internet). Thus, in one embodiment the transmitting unit and the receiving unit are computers that are part of a computer network, and the transmitting unit has hardware and/or software for acquiring or converting the sequence information into a digital format and transmitting the sequence information to a receiving unit, for example through a computer network. In other embodiments the transmitting unit is a telephone or a keyboard and the operator can manually key in the biological sequence information. The transmitting unit can also be an electronic device that sends the message to the receiving unit in any format (e.g., HTML). The format of data encoding and transmission can be any convenient format that can be converted by the receiving unit into instructions for synthesis of the biological sequence. The transmitting unit can obtain the information from a person that enters the information or can obtain it in an automated fashion from an instrument that determines the sequence. The source of the biological sequence information can be a sample of the virus or other biological entity.

The biological sequence information can be a series of nucleotides, phosphoramidites (e.g., nucleoside phosphoramidites), amino acids, or any sequence providing the information necessary to synthesize the primary structure of a biological entity. The biological sequence information can also be provided as a code that can be deciphered to arrive at the information necessary to synthesize the primary structure of the biological entity.

It is often the case that the sequence of a biological entity (e.g., a virus) will be deciphered at a scientific facility with special expertise in this technical area. DNA sequencing technology is widely known in the art and various methods of isolating DNA and performing sequencing are available. Thus, the sequence can be deciphered using standard, known technologies such as, for example, sequencing by synthesis, the dideoxy or chain termination (Sanger) method, the chemical degradation method, thermal cycle sequencing, pyrosequencing, or sequencing by hybridization. These are only some examples of DNA sequencing methods as persons of ordinary skill in the art are aware of numerous additional methods. The precise method of sequencing is not important, only that the sequence of the biological entity is acquired by the transmitting unit for transmission to a receiving unit from the transmitting unit. The sequence can be deciphered and can also be a predicted sequence, which predicted sequence can be based on trends or information derived from year to year changes in a virus. The year to year changes in the virus can be, for example, changes over a period of at least 2 years or at least 3 years or at least 5 years or at least 10 years.

In one embodiment the transmitting unit can also comprise or be associated with a DNA sequencer, or have the capacity to sequence DNA. Therefore a transmitting unit can have the capacity to determine the DNA sequence of an organism or biological sample and transmit the biological sequence information to a receiving unit at a remote location. Therefore the system and methods of the invention can have a sample return capability from remote locations, including locations outside of the Earth's atmosphere, such as the Moon or other planets.

Assembly Unit

The assembly unit synthesizes the biological sequence according to the information received by the receiving unit from the transmitting unit. The assembly unit deployed in the system of the invention can be connected to the receiving unit. As with the other system components the connection can be either a direct connection between the units, or can be an indirect connection through one or more additional computers, routers, or other electronic devices interposed between the units. The assembly unit can be in communication with the receiving unit so that, when the receiving unit receives the signal containing the biological sequence information from the transmitting unit, the information is provided to the assembly unit, which can immediately begin to synthesize the sequence in an automated method. The assembly unit can have various functions including, but not limited to, one or more of the synthesis of a nucleic acid molecule, the amplification of a nucleic acid molecule, and the transcription and/or translation of a nucleic acid molecule into a peptide or protein.

In some embodiments the assembly unit has the ability to perform a second (or third or fourth) level of biological assembly, e.g., the assembly of biological entities produced into larger biological entities. Thus, in one embodiment the assembly unit can synthesize oligonucleotides in an automated method, and then subsequently assemble the oligonucleotides into a larger dsDNA molecule. In one embodiment the oligonucleotides synthesized can be fragments of a DNA molecule of interest, or portions or variants of a DNA molecule of interest. The oligonucleotides can be assembled in combinatorial fashion, either sequentially or simultaneously as desired. A typical oligonucleotide can be from 40-100 nucleotides or from 30-110 nucleotides or from 50-90 nucleotides or about 60 nucleotides. But in various other embodiments the DNA molecules produced by the assembly unit can be greater than 100 bp, or greater than 200 bp, or greater than 300 bp, or greater than 400 bp, or greater than 500 bp, or greater than 600 bp, or greater than 700 bp, or greater than 800 bp, or greater than 900 bp, or greater than 1000 bp or from 100-1000 bp or from 200-1000 bp or from 300-1000 bp or from 400-1000 bp or from 500-1000 bp or from 600-1000 bp or from 700-1000 bp. The lengths recited can be the lengths with or without single-stranded overhangs (i.e., "sticky ends").

In various embodiments the assembly unit comprises one or more sub-units of a nucleic acid synthesizer, a protein and peptide synthesizer, a PCR thermocycler, and one or more sub-units for performing in vitro transcription and/or translation on a sample. Another sub-unit can be provided for incubating a biological entity in a cell culture and/or for maintaining cells in a cell culture.

Any one or any combination of the sub-units or all of the sub-units of the assembly unit can be automated. The systems of the invention can include an automated nucleic acid and/or amino acid synthesizer. The assembly unit of the invention can contain a plurality of vessels or containers having the chemicals, reagents, biological building blocks, or building block polymers necessary to perform nucleic acid or protein and peptide synthesis, and valves necessary to permit or restrict the flow of reagents, as well as vessels for conducting certain chemical reactions. These can also be present outside the assembly unit with passages providing the assembly unit access to them. The biological building block molecules can be, for example, amino acids, dNTPs, and/or nucleoside phosphoramidites necessary for synthesis of the desired biological sequence. The biological building blocks can also include monosaccharides, disaccharides, or polysaccharides. When the biological entity or biological product comprises more than one type of molecule, for example a glycoprotein, the biological building blocks will comprise amino acids and mono-, di-, or poly-saccharides as desired. Oligonucleotides or other building block polymers that are already assembled can also be provided in the vessels or containers.

The biological building blocks can also be modified, derivatized, or labeled. For example the biological building blocks can be nucleoside phosphoramidites or nucleoside triphosphates (NTPs), or derivatives of either. In various embodiments the modified, derivatized, or labeled building blocks can be aminoallyl, biotin, or 2' fluoro-modified or labeled NTPs or phosphoramidites. Additional modified, derivatized, or labeled building blocks include 2-aminopurine, 2,6-diaminopurine, 5-bromo deoxyuridine, inverted dT (prevents unwanted 5' ligations), dideoxycytidine, 5-methyl dC, deoxyinosine, 5-nitroindole, hydroxymethyl dC, Iso dC and iso dG, or locked nucleic acids to improve stability where desired. The assembly unit can contain the vessels that contain the chemicals, reagents, or biological building blocks, or the vessels can be outside the assembly unit and be connected to the assembly unit, for example via tubes or other pathways that carry the materials. The instruments typically contain software programming instructions necessary to control the instrument and synthesize a nucleic acid or protein/peptide in an automated fashion. Thus, the software programming instructions can be instructions directing the manipulations of the parts of the assembly unit to synthesize a set of oligonucleotides from biological building blocks (e.g., dNTPs or nucleoside phosphoramidites) according to the biological sequence information, and/or can include instructions for assembling the oligonucleotides into larger DNA molecules, and can further include instructions for transcribing the DNA molecules into RNA and for translating the RNA into protein molecules, and can further include instructions for assembling protein molecules into larger protein structures. In one embodiment the instructions are for assembling oligonucleotides into DNA or RNA molecules. In one embodiment the instructions are for assembling protein molecules into a virus or portion of a virus. And in another embodiment the system includes programming instructions for performing steps of an automated method in distinct zones of a reaction container.

The assembly unit can be a single, unitary unit, or can have various sub-units that perform the different functions. Thus, in one embodiment a sub-unit of the assembly unit performs oligonucleotide synthesis, for example with an oligonucleotide synthesizer. A robotic arm can be included to perform transfer of the reaction container (e.g., a 96 well plate) from the synthesizer to a liquid handler with thermocycling capabilities. Synthesized oligonucleotides can also be provided to another reaction container, or another zone of the same reaction container or to another sub-unit of the assembly unit for amplification, for example to a PCR thermocycler, and/or assembly. In one embodiment the system is provided with already synthesized oligonucleotides and assembles the oligonucleotides into one or more DNA molecules. And one or more other sub-units can perform transcription and/or translation of the synthesized nucleic acid into protein product, such as an automated in vitro translation system, or these functions too can be performed in another zone of the same reaction container. In each case the sub-units are prepared with the necessary reagents, chemical, and biological building blocks to perform the function in an automated manner. Thus, the assembly unit can begin to perform one or all of the functions immediately upon being provided with the biological sequence information from the receiving unit.

The assembly unit synthesizes the biological sequence according to the information received by the receiving unit from the transmitting unit or according to sequence information otherwise provided to the assembly unit. The assembly unit can thus in an automated fashion direct the synthesis of the desired biological entity. All of the units in the system, including the assembly unit, can be prepared with necessary software and pre-charged with necessary reagents and chemicals in the required vessels so that the biological sequence information can be received by the receiving unit and the assembly unit can instantly begin synthesizing the desired biological entity. Thus, the assembly unit can be prepared for assembly or synthesis of the biological entity prior to receiving the biological sequence information.

Following synthesis of oligonucleotides or peptides the assembly unit can also have the capability to assemble oligonucleotides into larger nucleic acid molecules and, respectively, peptides into polypeptides and proteins. The systems and methods can also assemble DNA molecules from oligonucleotides. Thus, the nucleic acid molecule or protein or peptide can be assembled through a series of reactions. In one embodiment for nucleic acid molecules the GIBSON ASSEMBLY® (Synthetic Genomics, San Diego, Calif.) reaction is used to assemble the nucleic acids, but in other embodiments any suitable method of assembling oligonucleotides (or peptides) into larger nucleic acids (or polypeptides) can be employed. The oligonucleotides can also be assembled into double-stranded nucleic acid molecules. Persons of ordinary skill are also aware of methods of assembling peptides into polypeptides and proteins, which can also be applied in the invention.

The assembly unit, or sub-units thereof, comprise one or more vessels that contain reagents, chemicals, biological building blocks, or building block polymers useful for performing the function of the assembly unit or sub-unit thereof. The vessels can be containers made of glass or another suitable material and can be pre-filled by the user prior to the receiving unit receiving the biological sequence information from the transmitting unit. Thus, the assembly unit can be set up and waiting to receive the biological sequence information from the transmitting unit. In some embodiments the functions of the assembly unit or sub-sets thereof will be managed and orchestrated by appropriate software that will direct the combination of materials from the various vessels. Each sub-unit of the assembly unit can operate from its own software upon receipt of the required information or the assembly unit can have one program that directs the various sub-units that may comprise the assembly unit.

In vitro and/or in vivo transcription and translation can be performed using a variety of methods known to persons of ordinary skill. In different protocols extracts of rabbit reticulocytes, wheat germ, E. coli, as well as human cell lysates are used in the synthesis of proteins. Human in vitro translation systems can be useful when the biological entity is a vaccine for use against human pathogens. The extracts can be prepared and contain the essential components of cellular translational machinery such as, for example, ribosomes, tRNAs, aminoacyl-tRNA synthetases, initiation, elongation, and termination factors, energy sources such as ATPs, necessary co-factors and other proteins. In vitro transcription and translation reactions can be performed at great speed and at the microliter or nanoliter level. A variety of commercially available kits can also be used for convenient set-up and have been used with success but the essential components can also be assembled generically. Whether kits or generic materials are used, in some embodiments a cell-free solution containing essential components of the cellular translational machinery is utilized.

In one in vitro translation method extracts of an immortalized human cell line are used to provide the ribosomes, initiation and elongation factors, tRNAs and the other basic components required for protein synthesis. Some systems utilize proprietary accessory proteins, ATP, and an energy regenerating system to sustain the synthesis of target proteins from DNA templates. The extracts can be prepared and pre-charged into a vessel of the assembly unit and be available to perform translation of synthesized nucleic acid when needed. The assembly unit can maintain these extracts at required temperatures to extend their useful life. The vessel or vessels for performing transcription and/or translation can also be linked to the vessels where DNA will be synthesized and amplified using PCR, and then transcribed into RNA. Upon transcription of RNA a portion of the reaction can be transferred into the vessel for performing translation, or the transcription and translation reactions can be performed in a single vessel. In some embodiments the biological entity requires protein modifications, such as glycosylated residues, a refolding step, or enzymatic modifications that must occur prior to the biological entity having activity or full activity. Reagents and programming protocols can be included within the assembly unit for this purpose as well.

All of these reactions can be performed in the reaction container itself within particular reaction areas or zones. The systems of the invention can also include sub-units, reaction areas, or reaction zones for the purification of biological products.

In one aspect the invention provides a system for the synthesis of a functional biological entity according to provided biological sequence information. The system has an assembly unit for assembling the biological entity according to the provided biological sequence information. The assembly unit contains or is connected to vessels containing biological building block molecules or building block polymers and has components for transporting reagents within the system and for executing steps in an automated method of the invention for synthesizing the functional biological entity. These systems can also have any of the components or features described herein. The biological entity can be any as described herein (e.g., a DNA molecule). The system can have a receiving unit for receiving a signal or data having the biological sequence information. The biological sequence information can be provided by manually keying in the sequence via an electronic interface, or by transmitting the sequence to a receiving unit from a transmitting unit, as described herein.

Biological Entity

The biological entity is a polynucleotide or DNA molecule, or a polyribonucleotide or an RNA molecule, or a peptide or polypeptide or protein. In some embodiments the biological entity is a nucleic acid or a DNA molecule. When the biological entity is a DNA or RNA molecule it can be convertible into a biological product. The DNA or RNA can be single-stranded DNA or RNA, or double-stranded DNA or RNA. When the biological entity is a DNA molecule it can be a functional DNA molecule, meaning that it can be transcribed into an RNA that can be translated into a functional protein or peptide, or is directly useful as a DNA molecule (e.g., as a DNA vaccine). A functional RNA molecule can be translated into a functional protein or peptide. A functional protein or peptide is one that has a clinical use in the treatment of a disease or disorder, or is directly useful in some biological context (e.g., as a structural protein or is useful as an enzyme). In various embodiments the functional protein or peptide can be the domain of a protein, a binding subunit, an enzyme or enzyme subunit that has enzymatic activity, a protein or peptide that has antigenic activity that is useful in the generation of a vaccine, a viral protein or a subunit thereof, a viral coat protein (e.g., an HA or NA protein), or a plurality of proteins or peptides that form a viral particle when combined in vitro or when combined in vitro in host cells. The clinical use can thus be the generation of an antigenic response or the binding of a protein or peptide to a specific binding molecule or receptor but in one embodiment the antigenic response is one that furthers the treatment of a disease or disorder (e.g., the generation of a vaccine to influenza) or finds use in an assay to identify the presence of an epitope. The functional protein or peptide can also provide a desirable property such as, for example, a desirable taste, texture, scent, or another property. In one embodiment a functional protein or peptide has a function other than the generation of an immune or antigenic response.

The biological entity can be of any size. Oligonucleotides of up to about 200 bp can be assembled but greater accuracy can often be achieved by synthesizing smaller oligonucleotides. In various embodiments the biological entity is a single-stranded or double-stranded DNA molecule of greater than 100 base pairs in length, or greater than 200 bp, or greater than 300 bp, or greater than 400 bp, or greater than 500 bp, or greater than 1 kb, or greater than 2.5 kb or greater than 3 kb or greater than 4 kb or greater than 5 kb or greater than 6 kb or greater than 7 kb or greater than 8 kb or greater than 9 kb or 1-10 kb or 1-9 kb or 1-8 kb or 2-10 kb or 2-9 kb or 2-8 kb. Using additional techniques the person of ordinary skill with resort to the present disclosure will realize that DNA sequences synthesized as oligonucleotides can also be joined to assemble a DNA molecule using the method described herein of greater than 1 kb, or greater than 2 kb, or greater than 3 kb, or greater than 5 kb, or greater than 6 kb or greater than 7 kb. In other embodiments the system and method of the invention can be used to assemble a DNA molecule of greater than 100 kb, or greater than 200 kb, or less than 200 kb, or greater than 300 kb, or less than 300 kb, or greater than 500 kb, or greater than 800 kb or greater than 1 mega-base or less than 1 mega-base.

Biological sequence information is that sequence information necessary for the synthesis of a biological entity, for example a nucleic acid, peptide, or protein. In some embodiments the biological sequence information is the sequence (or order) of nucleotides, amino acids, or other building block that comprises the primary structure of the nucleic acid or peptide or protein that is the biological entity. In different embodiments this information may be provided to the receiving unit in a binary form or in another encoded form.

Biological Product

A biological product is a biological molecule that is synthesized or assembled using the sequence information provided by the biological entity. Thus, in different embodiments the biological entity is a DNA molecule or an RNA molecule and the biological product can be any biological product made therefrom such as, for example, a viral genome or a portion thereof, a viral particle or viral coat or a portion of either, a bacteriophage or portion thereof, an antigenic portion of a viral particle or viral coat, a bacterial genome or portion thereof, a gene, a nucleic acid sequence, a single-stranded DNA molecule (ssDNA), a double-stranded DNA molecule (dsDNA), an RNA molecule, an anti-sense RNA moiety, an siRNA moiety, an RNAi moiety, a double-stranded RNA moiety, a protein molecule or protein moiety, a protein antigen or portion thereof, an enzyme, a structural protein, a regulatory protein, a nutritional protein, a binding protein, a transport protein, a peptide molecule, a gene or genome of a fungus or portion thereof, or a synthetic cell. The biological product can also be a protein, peptide, or polypeptide that has undergone modification such as, for example, glycosylation of certain amino acid residues to produce a glycoprotein, or another molecule formed of two or more biological building blocks. In other embodiments the biological product is a genome of a synthetic bacteria or a portion thereof. In a particular embodiment the biological product is an influenza virus and the sequence information is information that is used to prepare a vaccine against the biological threat. When the biological product is a virus or virus particle, it can be an attenuated virus or a killed virus or a harmless virus. In some embodiments the biological entity itself can also be the biological product. An example of when the biological entity is the biological product is a DNA vaccine, where the DNA molecule itself is useful as a vaccine. DNA vaccines are comprised of pieces of DNA that code for pathogen proteins. After injection into the body the host cells synthesize the pathogen proteins, stimulating an immune response. In one embodiment the biological entity is a plurality of single-stranded DNA (ssDNA) or oligonucleotides that can be assembled into a double-stranded DNA (dsDNA). A "portion" of a molecule, virus, or other biological entity can be at least 10% or at least 20% or at least 30% or at least 40% or at least 50% or at least 60% or at least 70% or at least 80% or at least 90% of the native molecule or biological entity.

In some embodiments the action of a host cell can be utilized to arrive at the biological product. In systems and methods where host cells are used they can be located within a subunit of the assembly unit that can receive a biological entity from another subunit for further processing, or can simply be maintained in a zone of the reaction container. For example the host cells can be maintained in a vessel within the subunit. Host cells are useful in the systems and methods of the invention for a variety of purposes. While in vitro translation can be used in the systems and methods of the invention, transcription, translation, and assembly of molecular sub-units can also be performed by host cells. Host cells can also be used to receive a biological entity and use it to synthesize a biological product. In one embodiment host cells are transfected with multiple DNAs, which are biological entities synthesized by a subunit of the assembly unit. The host cells can use the DNAs to make proteins within the host cells and/or to assemble the proteins into a biological product, for example a viral particle or portion thereof, or a protein or enzyme having multiple subunits. Host cells may also be used to replicate phage or viral particles following infection or transfection.

Methods

The invention provides methods of synthesizing a functional biological entity. In the invention a digital DNA sequence or coded sequence can be entered into a software program that automatically designs a synthesis paradigm for the received DNA sequence (e.g., ARCHETYPE®, Synthetic Genomics, San Diego, Calif.). The software can break the sequence into designed overlapping oligonucleotides of, for example, about 50-80 bases or about 40-90 bases or about 30-100 bases or about 30-60 bases or about 30-80 bases or 20-100 bases or 20-80 bases or 10-100 bases or 10-90 bases or 10-80 bases, and any of these sizes can be used as the oligonucleotides of the invention. The oligonucleotide sequences are then transmitted to the sub-units of the system for assembly. In a particular embodiment the software can design the oligonucleotides to contain an overlap of about 30 bp (±5% or ±10%) between adjacent oligonucleotides (ssDNA) of about 60 bp. The oligonucleotides can also be designed to have universal primer-binding domains for PCR amplification and restriction sites to release the primer-binding domains following the PCR amplification. The software used in the invention can also have the ability to modify received or desired sequence into codon-optimized sequences tailored to a particular host organism to be used in the method. The software can be present in any unit or sub-unit of the system.

The methods can be conducted on one or more samples that are situated in one or more reaction areas of a reaction container. In some embodiments the reaction container is a reaction plate. An example of a reaction plate is a 96 well plate, but it will be realized that the methods can be conducted on a reaction container having any number of reaction areas. When the reaction container is a reaction plate it can have any convenient number of reaction wells (areas), such as the 96 reaction wells on a standard 96 well plate. In some embodiments the methods involve one or more steps of transporting a sample from one zone of a vessel to a second zone of the vessel.

In some embodiments the method can be completed on a single reaction container. These embodiments can involve dividing the reaction container into reaction zones, and transporting one or more samples from one zone of the reaction container to a second zone of the reaction container to perform distinct steps of a method, but can also involve leaving all or a portion of the sample in place and moving the reaction container so that one or more zones of the reaction container are exposed to a different environment. For example, in a step involving PCR the zone can be located at a point in the system where it is exposed to a thermocycling schedule. At a DNA assembly step the reaction container can be located at another point in the system where it is exposed to the conditions appropriate for DNA assembly. The change of location can be accomplished by a physical movement of the reaction container or, alternatively, by a movement of one or more units of the system. The reaction container is thus moved relative to the system of the invention.

A zone of a reaction container is a distinct area of a reaction container containing one or more reaction areas where sample is collected. Normally each zone of a reaction container will contain multiple reaction areas, such as the wells in a reaction plate. But a reaction area does not require a physical barrier or boundary—it requires only that a distinct reaction can be carried out in the reaction area relative to other reaction areas. A reaction container can have any number of zones but each zone has one or more reaction areas for collecting and holding a sample. Each zone of a reaction container is treated in the same manner or subjected to the same treatment or process in a given time period. For example the samples present in a zone may all be cycled at the same temperature of a PCR cycle being executed on that zone of the reaction container, or all reaction samples in a reaction zone may be picked up in automated fashion and moved to another zone on the same reaction container.

Thus in one embodiment of the methods a PCR step is performed in a first reaction zone of the reaction container and an error correction step is performed in a second zone of the reaction container, and a 2nd PCR step is performed in a third reaction zone of a reaction container. The methods can also have a step of DNA assembly performed in another reaction zone of the reaction container, and a transcription step performed in another reaction zone of the reaction container, and a translation step performed in another reaction zone of the reaction container, and a transfection step performed in another reaction zone of the reaction container. Thus, each step of any of the methods described herein can be performed in a distinct reaction zone of a reaction container.

Kits

The invention further provides kits for use in the systems and methods of the invention. The kits can contain reagents and components necessary to assemble a biological product, such as any combination of biological building blocks, building block polymers, buffers, or other reagents for carrying out a method of the invention on a system of the invention. Either alone or with any combination of the above reagents and components, the kits can also contain a reaction container for performing methods of the invention. Any combination of the reagents or reaction components or reaction containers can be provided in a container having the members of the kit. Reagents and reagent components can also be provided in a reagent vessel that fits onto an interface of a system of the invention.

The kits can also include one or more reaction containers that have been designed to fit onto an interface of a system of the invention and the reaction containers can be prepared or pre-charged with reagents and/or biological building blocks and/or building block polymers necessary for the synthesis of a biological entity using a system of the invention. The kits can also contain instructions for attaching the reaction containers or reagent vessels to a system of the invention and/or instructions for using the reaction containers or reagent vessels in a method of the invention. The instructions can also be provided on a website and the kit can include a link to the website, either instead of or in addition to the instructions provided with the kit.

Any of the kits of the invention can also include instructions for conducting an assay of the invention and/or a link to a website providing the same information or information for preparing and/or using a system of the invention to synthesize a biological entity and/or for preparing or pre-charging vessels with reagents, components, and/or biological building blocks necessary to synthesize a biological entity. For example, the instructions can provide guidance on the type and quantity of reagents to be used in the systems and methods. The kits can be provided or packaged in a single container or in multiple containers. The vessels can be made of glass, plastic or any suitable material, and may also be sterile. One or more vessels can be provided in a sterile container within the container comprising the kit.

Additional Aspects of the Systems

The systems of the invention can produce a biological entity by carrying out an automated method. The biological entity can be any desired sequence. In one embodiment the systems of the invention can be pre-programmed to include desired sequences or constructs as part of the biological entity. For example the systems of the invention can be pre-programmed to enable the operator to append a particular sequence to be synthesized to a plasmid or other vector desirable for the further use of the synthesized sequence. In other embodiments the systems can synthesize a requested sequence and append regulatory sequences or promoter sequences or binding elements for trans-acting factors, or signal sequences to the requested sequence as part of the biological entity. Thus, when the operator knows that a sequence will be synthesized for later use in a particular host organism, the system can synthesize the requested sequences with the regulatory sequences or other desirable sequences particular to the host organism, thus further simplifying and speeding the preparation of the biological entity or biological product. In addition to being synthesized by the systems and methods of the invention the regulatory sequences, promoter sequences, signal sequences, and binding elements for trans-acting factors can also be pre-charged into reagent vessels and/or reaction containers of the invention as pre-made sequences for use as desired. These pre-made sequences can also be included in any kit of the invention.

In one embodiment the systems of the invention are programmed to perform biosecurity screening in order to identify prohibited sequences. The biosecurity screening is done by comparing the sequence the system has received (in all 6 reading frames) and is requested to synthesize against a pre-programmed database of prohibited sequences. The prohibited sequences can be derived from a list of pathogens, biological weapons, or other biosecurity threats that are prohibited by a local government from being synthesized. The prohibited sequences can be one or more of DNA or RNA or proteins or peptides. The system can be programmed so that if a sequence is received that is identified on the list of prohibited sequences the system will be rendered inoperative or will otherwise not synthesis a prohibited sequence. Prohibited sequences can also be obtained from the International Gene Synthesis Consortium. The system can also screen against protein sequences derived from a prohibited sequences list.

Some embodiments of the systems of the invention perform modifications to DNA after synthesis, for example in a sub-unit of the system. In other embodiments the systems can also perform post-transcriptional and/or post-translational modifications. In one embodiment the system produces a DNA molecule, which can then be modified to produce a modified DNA molecule. In one embodiment the modification is the methylation of DNA at particular nucleotides or nucleotide analogs. In another embodiment a sub-unit of the invention can contain methyltransferases and/or have the capacity to perform phosphorylation or dephosphorylation on biological entities or biological products of the invention. 2' fluoro and 2' O-methyl NTPs can also be produced enzymatically or chemically by the system to improve in vivo stability of DNA or RNA. In another embodiment the system produces a requested RNA molecule and adds a 7-methylguanosine residue to the 5' end as a 5' cap or a 5'-5' phosphate linkage as a cap, which the system can then methylate to form mature mCAP. Guanosine-5'-triphosphate-5' guanosine can also be used as an RNA cap. RNA bases can also be post-transcriptionally modified by the systems using a 2' O-methyl group to increase melting temperature and increase stability. In another embodiment the system produces a requested RNA molecule having a poly-A tail, with any number of A residues. Other embodiments include the inclusion of cleavage signals or sequences, or GU-rich sequences in the biological entity, which also can be tailored to a particular host cell to be used in a subsequent procedure. In still more embodiments the systems of the invention produce a requested peptide, polypeptide or protein sequence with Example 1

Synthesis of a Functional HA and NA DNA Molecules and Protein Moieties

Figure 2A:
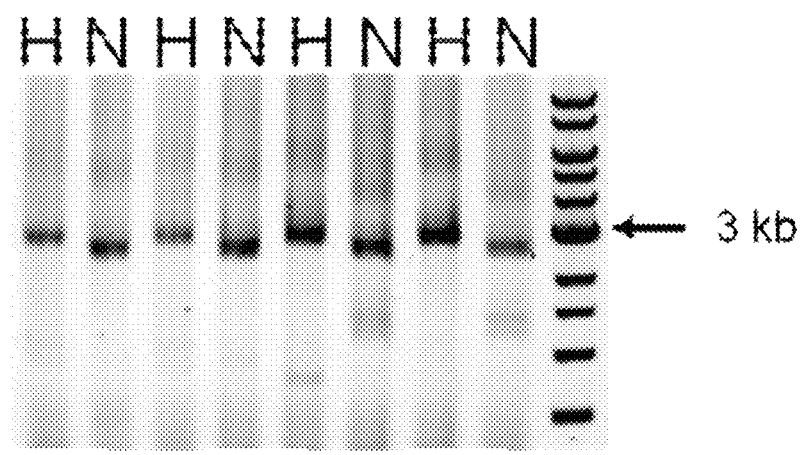
FIGS. 2A and 2B illustrate a 0.8% pre-cast agarose gel showing the assembly of nucleic acid constructs HA (H) and NA (N) from various influenza virus strains, each assembled from 96 pooled oligonucleotides in a system of the invention using the methods of the invention. Both Constructs HA and NA are of approximately 3 kb.
Figure 2B:
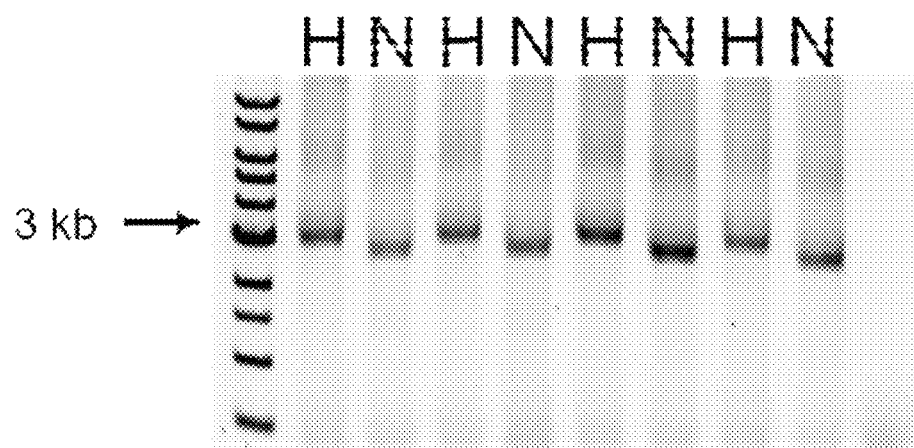

This example illustrates the automated assembly of DNA constructs of HA and NA genes from an oligonucleotide pool and their transfection into a host cell that produces viral particles. Influenza viruses are made of a viral envelope containing glycoproteins wrapped around a central core. The central core contains the viral RNA genome and other viral proteins that package and protect the RNA. The influenza genome typically contains eight pieces of RNA with each containing one or two genes encoding viral proteins. In the case of influenza A, the genome contains 11 genes on eight pieces of RNA, encoding for 11 proteins, including hemagglutinin (HA) and neuraminidase (NA). Other proteins include nucleoprotein (NP), M1, M2, NS1, NS2, PA, PB1, PB1-F2 and PB2.

Hemagglutinin (HA) and neuraminidase (NA) are glycoproteins present on the outside of the viral particles. These glycoproteins have key functions in the life cycle of the virus, including assisting in binding to host cells and reproduction of viral particles. The assembled virus containing these proteins is therefore useful in the production of a vaccine.

Oligonucleotide Synthesis and Assembly

A pool of 96 oligonucleotides representing the sequence of DNA constructs of the HA and NA genes were provided to an assembly unit of the invention. The HA and NA constructs were approximately 3 kb in length and were assembled from 96 oligonucleotides in the method. The first and last oligonucleotides contained primer binding domains for PCR amplification and NotI restriction sites to release the primer binding domains following amplification and expose overlapping regions for DNA assembly, if necessary to assemble larger fragments.

The assembly unit utilized a BIOMEK® NXP, Span-8 laboratory automation workstation (Beckman Instruments Inc., Fullerton, Calif.) with integrated thermal-cycling capabilities.

The assembly unit was programmed to perform several different steps in the process namely, 1) PRC1 amplification to amplify oligonucleotides; 2) an error correction step on the PCR1 amplified oligonucleotides; 3) a PCR2 step to amplify the corrected oligonucleotides; 4) a PCR product purification step to provide pure amplified oligonucleotides; 5) an assembly step to assemble the oligonucleotide products into a gene. Each process can be performed in a distinct reaction zone of the reaction container (which is a 96 well plate), and the reaction zone can be one or more columns on the 96 well plate. Assembly reaction is at 50° C. for 30-60 minutes and the reaction is temperature shifted and held at 10° C. thereafter.

1st PCR and Error Correction

1. For each assembled product PCR reactions were performed in automated fashion:

25 μl 2×PHUSION® Hot-Start Master Mix (Thermo Fisher Scientific Oy, Oy, Fl)

2 μl 1% PEG 8000

0.25 µl Terminal Primer 1 (100 uM)
0.25 µl Terminal Primer 2 (100 uM)
20 µl MBG water
2.5 µl of the oligo pool above was transferred at 50 nM as template to a reaction zone of the reaction container containing PCR master mix (or combine subsequently).
2. Thermal-cycle occurred using the following parameters:
98° C. for 1 min
30×(98° C. 30 sec, 65 C 6 minutes and extending that by 15 sec/cycle
72° C. for 5 min
10° C. forever
Error Correction
Denaturation/annealling by thermocycling using the following parameters:
98° C. for 2 min
2° C./sec to 85° C.
85° C. for 2 min
0.1° C./sec to 25 C
25° C. 2 min
10° C. forever
2.7 µl was removed and added to 8.3 ul of error correction mix comprising 5.3 ul water/2 ul SURVEYOR™ nuclease (Transgenomic, Inc., Omaha, Nebr.)/1 ul 1:4000 diluted Exo III.
Thermo-cycled at 42° C. for 1 hour, 10° C. forever
2nd PCR
See above for Master Mix recipe.
2.5 µl of error-corrected sample was used in a 50 ul total reaction volume.
See above for the thermal cycler conditions.
PCR Purification
PCR product was purified using the AMPURE® XP technology (Agencourt, Bioscience Corp. Beverly, Mass.)
GIBSON ASSEMBLY® (Synthetic Genomics, San Diego, Calif.) to Combine Sub-Assemblies into HA and NA Genes within Plasmid Vectors
Nucleic acid constructs of approximately 3 kb were produced. The electrophoretic gels are shown in FIG. 2. These genes already include promoter regions (pol I and pol II) for expression following transfection into mammalian cells.
Genes were cloned into pUC19 using GIBSON ASSEMBLY® mix with the vector.
The following were combined:
5 µl of mix
5 µl of DNA amplicon
The mix was incubated within the reaction container on the thermo-cycler 50° C. for 1 hour, then 10° C. forever.
Transform Plasmid Vector DNA to Host Cells
The next step is to combine the genes with the constant influenza genes to provide the complete viral genome. The genes are then transfected into MDCK cells to produce a rescued virus. The cells then produce the virus product, which is ready for harvest.

Example 2

Generation of Immunological Response

In a further experiment sequences were synthesized in a manner as described in Example 1 for the influenza A/Shanghai/2/2013 HA gene. The synthetic HA sequences were cloned into a DNA template containing RNA-dependent RNA polymerase genes, genetic control elements, and a T7 polymerase promoter according to previously described self-amplifying RNA vaccine technology (Geall et al., Non-viral delivery of self-amplifying RNA vaccines, PNAS, Vol. 109, No. 36, pp. 14604-09 (2012)). After verification of the construct in vitro transcription of the RNA, capping of the RNA, and transfection of BHK cells with the RNA was carried out. The integrity of the transcribed RNA was demonstrated by agarose gel electrophoresis (not shown). The cells expressed the H7 HA, as demonstrated by gel electrophoresis and Western blot with an H7-specific antibody. The RNA was encapsulated in a lipid nanoparticle (LNP) delivery system and the vaccine was used to immunize mice (Geall et al., and Hekele et al., Emerging Microbes and Infections (2013) 2, e52). Two weeks after the first injection, six of seven H7/LNP-immunized mice seroconverted with H7-specific hemagglutinin inhibition titers ranging from 1:20 to 1:80 (data not shown).

Example 3

Synthesis of a Functional Phage Particle and Oligonucleotide Design

The present invention can be applied to the production of a phage, which can be useful in phage therapy. In one embodiment the phage is a bacteriophage. Phage therapy is useful for the treatment of pathogenic bacterial infections, in humans, animals, and plants. Phage therapy can be particularly useful in applications where the bacteria does not respond to convention methods of control.

The 5,386 bp PhiX DNA biological sequence is entered into a transmitting unit of the invention using ARCHETYPE® software (Synthetic Genomics, Inc., San Diego, Calif.) (Ref. Seq: NC_001422, sequence below) at a laboratory. The software divides the sequence into four overlapping fragments of about 1.4 kb each (sub-assemblies of the PhiX genome sequence). Each fragment overlaps the next by 40 bp to form a circular molecule when assembled. Each of the four fragments is further divided into 43-45 overlapping oligonucleotides. These oligonucleotides are about 64 bases in length with 32 bp overlaps. The first and last oligonucleotides of each of the four overlapping fragments contain primer binding domains for PCR amplification and NotI restriction sites to release the primer binding domains, following amplification, and expose overlapping regions for DNA assembly. Following entry the biological sequence information is transmitted to a receiving unit located in a laboratory in a remote city.

Oligonucleotide Synthesis

The biological sequence information is received by a receiving unit of the invention, which in this embodiment is a computer connected to the same computer network as the transmitting unit. The receiving unit is connected to an assembly unit, which in this embodiment also has a BIO-AUTOMATION™ 192E oligonucleotide synthesizer (Bio-Automation Corp., Plano, Tex.) as one sub-unit. All sub-units of the assembly unit are set up prior to receiving the biological sequence information. Setup includes, but is not limited to, charging all vessels with requisite chemicals, reagents, and biological building blocks, as well as preparing all software programming prior to receiving the biological sequence information so that activation of the synthesis of the biological entity can begin immediately upon receiving the sequence information. Each step of the method is performed in a distinct reaction zone of the reaction container.

After receipt of the biological sequence information, software within the assembly unit directs the synthesis of the oligonucleotides, which are synthesized using the biological building blocks previously provided to the system (in this case nucleoside phosphoramidite building blocks). This synthesis is performed on a sub-unit such as an oligonucleotide synthesizer.

After synthesis the oligonucleotides are cleaved from the solid support by the addition of concentrated ammonium hydroxide and incubated at 55° C., each step done in automated fashion without further human intervention after setup. Oligonucleotides making up each fragment are separately pooled and purified by passing through a column containing POLYPAK™ packing (Glen Research, Sterling, Va.). Other packings can also be used that are stable in the pH range 1-13. Thus, the ammonium hydroxide solution, diluted with water, is loaded directly onto the packing. After elution of failure sequences, the trityl protecting group is removed and washed from the support-bound oligonucleotide. The fully deprotected product can then be eluted and isolated by lyophilization. Deprotection procedures suitable for automation are used, for example on-column deprotection using Ethylenediamine (EDA)/Toluene solution. A paramagnetic bead-based purification system can also be used, an example of which is AGENCOURT® COSMCPREP® (Agencourt Bioscience Corp., Beverly, Mass.). Following the above procedure the four pools of oligonucleotides making up each of the four fragments required to produce overlapping dsDNA fragments of PhiX are produced.

GIBSON ASSEMBLY® (Synthetic Genomics, San Diego, Calif.) to Produce Four Overlapping PhiX Sub-Assemblies The following steps are also performed in automated fashion by the assembly unit, which can have as many sub-units as necessary and convenient. Each sub-unit of the assembly unit is pre-charged with reagents as necessary to perform all steps. After oligonucleotide assembly a robotic arm is used to transfer the reaction container from the oligo synthesizer to a liquid handler with thermo-cycling capabilities. In a fully automated fashion, 10 µl of each of the four oligonucleotide pools above are added to 10 ul of PCR assembly reagents—one can utilize a dilution of about 10 µM. A convenient form of PCR reagents is 2×HF PHUSION® Mix (Thermo Fisher Scientific Oy, Oy, Fl). The protocol is set forth below.

Assembly reaction is at 50° C. for 30-60 minutes and the reaction is temperature shifted and held at 10° C. thereafter.

1st PCR and Error Correction

1. For each assembled product PCR reactions are performed in automated fashion:
   25.00 µl 2×HF PHUSION® Mix (Thermo Fisher Scientific Oy, Oy, Fl)
   0.25 µl Terminal Primer 1 (100 µM)
   0.25 µl Terminal Primer 2 (100 µM)
   22 µl Water
   2.5 µl Template (GIBSON ASSEMBLY® (Synthetic Genomics, Inc., San Diego, Calif.) of the reaction product from above)
2. Thermal-cycle occurs using the following parameters:
   98° C. for 1 min
   Cycle 25×{98° C. for 10 sec, 60° C. for 30 sec., 72° C. for 1.5 min)
   72° C. for 5 min
   98° C. for 2 min
   Increase 2° C./sec to 85° C.
   85° C. for 2 min
   Decrease 0.1° C./sec to 25° C.
   25° C. for 2 min
   Hold at 10° C. thereafter 3. 6.25 µl of S/E error correction mix is added (protocol below) to each sample
4. Error correction reaction is at 42° C. for 1 hour and then the reaction is temperature shifted and held at 10° C. thereafter.

2nd PCR

1. The following four PCR reactions are also performed in automated fashion by the thermo-cycling sub-unit of the assembly unit:
   25.00 ul 2×HOTSTART-IT® Taq Master Mix (Affymetrix, Inc., Santa Clara, Calif.) or alternative (PHUSION® (Thermo Fisher Scientific Oy, Oy, Fl) per reaction
   0.25 µl Primer 1 (100 µM)
   0.25 µl Primer 2 (100 µM)
   22.00 µl MBG Water
   2.50 µl Error corrected template from above.

GIBSON ASSEMBLY™ (Synthetic Genomics, San Diego, Calif.) to Combine Four Sub-Assemblies into phiX Genome The following procedure is performed in automated fashion:
1. 2.5 µl of each of the four amplicons is removed from the 2nd PCR above and pooled into another coordinate of a 96-well plate.
2. 2 µl of NotI restriction enzyme is added and incubated at 37° C. for 1 hour, then 65° C. for 20 minutes to inactivate the NotI enzyme.
3. 12 µl 2×GIBSON ASSEMBLY™ (Synthetic Genomics, Inc., San Diego, Calif.) master mix is added and incubated at 50° C. for 1 hour.

Production of Active PhiX Virus

In this step active virus particles are produced. These steps are also performed in automated fashion. Following DNA synthesis and assembly as described above, the assembled ΦX174 genome is combined with chemically-competent *E. coli* strain C or another ΦX174-sensitive *E. coli* strain (e.g., DH10). Following the heat-shock at 42° C., cells are recovered in SOC medium.

1. 5 µl of assembly reaction above is combined with 50 µl of chemically competent DH10 *E. coli* cells in a vessel.
2. Thermal-cycling is performed according to the following conditions:
   4° C. for 2 min
   42° C. for 30 sec
   4° C. for 2 min
3. 150 µl SOC medium is added and cells are incubated at 37° C. for several hours Active phage particles are purified from *E. coli* and tested for capacity to form plaques when spread on LB agar plates containing *E. coli* cells (Smith et al, PNAS 2003).

As an alternative approach to transforming *E. coli* cells, it is also possible to test for the capacity to form active phage particles in a cell-free system. In this embodiment, synthetic genomes are incubated for 2 hours in one of the cell-free expression kits described above.

Reagent Components

Components for GIBSON ASSEMBLY® (Synthetic Genomics, Inc., San Diego, Calif.).
1. 5× isothermal (ISO) reaction buffer (25% PEG-8000, 500 mM Tris-HCl pH 8.0, 50 mM MgCl$_2$, 50 mM DTT, 1 mM each of the 4 dNTPs, and 5 mM NAD). This is prepared as described below.
2. T5 exonuclease
3. PHUSION® High Fidelity DNA polymerase (Thermo Fisher Scientific Oy, Oy, Fl)
4. Taq DNA ligase Procedure
1. 5×ISO buffer is prepared. Six ml of this buffer can be prepared by combining the following:
   3 ml of 1 M Tris-HCl pH 8.0
   300 µl of 1 M MgCl2
   600 µl of 10 mM dNTPs
   300 µl of 1 M DTT (1.54 g dissolved in dH20 up to 10 ml)
   1.5 g PEG-8000
   300 µl of 100 mM NAD (0.66 g dissolved in dH20 up to 10 ml; resuspend by heating at 50° C. followed by continuous vortexing)
   Water is added to 6 ml. Aliquot 1 ml and store at −20° C.
2. 800 µl of the assembly master mixture is prepared, sufficient for 80 reactions. This can be prepared by combining the following:
   320 µl 5×ISO buffer
   6.4 µl of 1 U/µl T5 exo (diluted 1:10 from enzyme stock in 1×T5 exo buffer)
   20 ul of 2 U/µl PHUSION® High Fidelity DNA polymerase (Thermo Fisher Scientific Oy, Oy, Fl)
   80 µl of 40 U/µl Taq ligase
   374 µl dH20
   The mixture is mixed well and stored at −20° C., or on ice if to be used immediately.
3. The assembly mixture can be stored at −20° C. for at least one year. The enzymes remain active following at least 10 freeze-thaw cycles.
The mixture is ideal for the assembly of DNA molecules with 20-150 bp overlaps.

Error Correction Mix Components-Surveyor Nuclease+ Exonuclease III (S/E)
   250 µl of SURVEYOR™ Nuclease (Transgenomic Inc., Omaha, Nebr.)+0.03125 µl Exonuclease III

| PhiX Genome Sequence |
| --- |
| SEQ ID NO: 5 |
| GAGTTTTATCGCTTCCATGACGCAGAAGTTAACACTTTCTGGATATTTCT |
| GATGAGTCGAAAAATTATCTTGATAAAGCAGGAATTACTACTGCTTGTT |
| TACGAATTAAATCGAAGTGGACTGCTGGCGGAAAATGAGAAAATTCGA |
| CCTATCCTTGCGCAGCTCGAGAAGCTCTTACTTTGCGACCTTTCGCCAT |
| CAACTAACGATTCTGTCAAAAACTGACGCGTTGGATGAGGAGAAGTGG |
| CTTAATATGCTTGGCACGTTCGTCAAGGACTGGTTTAGATATGAGTCAC |
| attttgttcatggtagagattctcttgttgacattttaaaagagcgtgg |
| ATTACTATCTGAGTCCGATGCTGTTCAACCACTAATAGGTAAGAAATCA |
| TGAGTCAAGTTACTGAACAATCCGTACGTTTCCAGACCGCTTTGGCCTC |
| TATTAAGCTCATTCAGGCTTCTGCCGTTTTGGATTTAACCGAAGATGAT |
| TTCGATTTTCTGACGAGTAACAAAGTTTGGATTGCTACTGACCGCTCTC |
| GTGCTCGTCGCTGCGTTGAGGCTTGCGTTTATGGTACGCTGGACTTTGT |
| GGGATACCCTCGCTTTCCTGCTCCTGTTGAGTTTATTGCTGCCGTCATTG |
| CTTATTATGTTCATCCCGTCAACATTCAAACGGCCTGTCTCATCATGGAA |
| AGGCGCTGAATTTACGGAAAACATTATTAATGGCGTCGAGCGTCCGGT |
| TAAAGCCGCTGAATTGTTCGCGTTTACCTTGCGTGTACGCGCAGGAAAC |
| ACTGACGTTCTTACTGACGCAGAAGAAAACGTGCGTCAAAAATTACGT |
| GCGGAAGGAGTGATGTAATGTCTAAAGGTAAAAACGTTCTGGCGCTC |
| GCCCTGGTCGTCCGCAGCCGTTGCGAGGTACTAAAGGCAAGCGTAAAG |
| GCGCTCGTCTTTGGTATGTAGGTGGTCAACAATTTTAATTGCAGGGGCT |
| TCGGCCCCTTACTTGAGGATAAATTATGTCTAATATTCAAACTGGCGCC |
| GAGCGTATGCCGCATGACCTTTCCCATCTTGGCTTCCTTGCTGGTCAGA |
| TTGGTCGTCTTATTACCATTTCAACTACTCCGGTTATCGCTGGCGACTCC |
| TTCGAGATGGACGCCGTTGGCGCTCTCCGTCTTTCTCCATTGCGTCGTG |
| GCCTTGCTATTGACTCTACTGTAGACATTTTTACTTTTTATGTCCCTCAT |
| CGTCACGTTTATGGTGAACAGTGGATTAAGTTCATGAAGGATGGTGTTA |
| ATGCCACTCCTCTCCCGACTGTTAACACTACTGGTTATATTGACCATGC |
| CGCTTTTCTTGGCACGATTAACCCTGATACCAATAAAATCCCTAAGCAT |
| TTGTTTCAGGGTTATTTGAATATCTATAACAACTATTTTAAAGCGCCGT |
| GGATGCCTGACCGTACCGAGGCTAACCCTAATGAGCTTAATCAAGATG |
| ATGCTCGTTATGGTTTCCGTTGCTGCCATCTCAAAACATTTGGACTGC |
| TCCGCTTCCTCCTGAGACTGAGCTTTCTCGCCAAATGACGACTTCTACC |
| ACATCTATTGACATTATGGGTCTGCAAGCTGCTTATGCTAATTTGCATA |
| CTGACCAAGAACGTGATTACTTCATGCAGCGTTACCATGATGTTATTTC |
| TTCATTTGGAGGTAAAACCTCTTATGACGCTGACAACCGTCCTTTACTT |

| PhiX Genome Sequence |
| --- |
| GTCATGCGCTCTAATCTCTGGGCATCTGGCTATGATGTTGATGGAACTG |
| ACCAAACGTCGTTAGGCCAGTTTTCTGGTCGTGTTCAACAGACCTATAA |
| ACATTCTGTGCCGCGTTTCTTTGTTCCTGAGCATGGCACTATGTTTACTC |
| TTGCGCTTGTTCGTTTTCCGCCTACTGCGACTAAAGAGATTCAGTACCTT |
| AACGCTAAAGGTGCTTTGACTTATACCGATATTGCTGGCGACCCTGTTT |
| TGTATGGCAACTTGCCGCCGCGTGAAATTTCTATGAAGGATGTTTTCCG |
| TTCTGGTGATTCGTCTAAGAAGTTTAAGATTGCTGAGGGTCAGTGGTAT |
| CGTTATGCGCCTTCGTATGTTTCTCCTGCTTATCACCTTCTTGAAGGCTT |
| CCCATTCATTCAGGAACCGCCTTCTGGTGATTTGCAAGAACGCGTACTT |
| ATTCGCCACCATGATTATGACCAGTGTTTCCAGTCCGTTCAGTTGTTGC |
| AGTGGAATAGTCAGGTTAAATTTAATGTGACCGTTTATCGCAATCTGCC |
| GACCACTCGCGATTCAATCATGACTTCGTGATAAAAGATTGAGTGTGA |
| GGTTATAACGCCGAAGCGGTAAAAATTTTAATTTTTGCCGCTGAGGGGT |
| TGACCAAGCGAAGCGCGGTAGGTTTTCTGCTTAGGAGTTTAATCATGTT |
| TCAGACTTTTATTTCTCGCCATAATTCAAACTTTTTTCTGATAAGCTGG |
| TTCTCACTTCTCTGTTACTCCAGCTTCTTCGGCACCTGTTTTACAGACACCT |
| AAAGCTACATCGTCAACGTTATATTTTGATAGTTTGACGGTTAATGCTA |
| GTAATGGTGGTTTTCTTCATTGCATTCAGATGGATACATCTGTCAACGC |
| CGCTAATCAGGTTGTTTCTGTTGGTGCTGATATTGCTTTTGATGCCGACC |
| CTAAATTTTTTGCCTGTTTGGTTCGCTTTGAGTCTTCTTCGGTTCCGACT |
| ACCCTCCCGACTGCCTATGATGTTTATCCTTTGAATGGTCGCCATGATG |
| GTGGTTATTATACCGTCAAGGACTGTGTGACTATTGACGTCCTTCCCCG |
| TACGCCGGGCAATAACGTTTATGTTGGTTTCATGGTTTGGTCTAACTTT |
| ACCGCTACTAAATGCCGCGGATTGGTTTCGCTGAATCAGGTTATTAAAG |
| AGATTATTTGTCTCCAGCCACTTAAGTGAGGTGATTTATGTTTGGTGCT |
| ATTGCTGGCGGTATTGCTTCTGCTCTTGCTGGTGGCGCCATGTCTAAATT |
| GTTTGGAGGCGGTCAAAAAGCCGCCTCCGGTGGCATTCAAGGTGATGT |
| GCTTGCTACCGATAACAATACTGTAGGCATGGGTGATGCTGGTATTAAA |
| TCTGCCATTCAAGGCTCTAATGTTCCTAACCCTGATGAGGCCGCCCCTA |
| GTTTTGTTTCTGGTGCTATGGCTAAAGCTGGTAAAGGACTTCTTGAAGG |
| TACGTTGCAGGCTGGCACTTCTGCCGTTTCTGATAAGTTGCTTGATTTG |
| GTTGGACTTGGTGGCAAGTCTGCCGCTGATAAAGGAAAGGATACTCGT |
| GATTATCTTGCTGCTGCATTTCCTGAGCTTAATGCTTGGGAGCGTGCTG |
| GTGCTGATGCTTCCTCTGCTGGTATGGTTGACGCCGGATTTGAGAATCA |
| AAAAGAGCTTACTAAAATGCAACTGGACAATCAGAAAGAGATTGCCGA |
| GATGCAAAATGAGACTCAAAAAGAGATTGCTGGCATTCAGTCGGCGAC |
| TTCACGCCAGAATACGAAAGACCAAGGTATATGCACAAAATGAGATGCT |
| TGCTTATCAACAGAAGGAGTCTACTGCTCGCGTTGCGTCTATTATGGAA |
| AACACCAATCTTTCCAAGCAACAGCAGGTTTCCGAGATTATGCGCCAA |
| ATGCTTACTCAAGCTCAAACGGCTGGTCAGTATTTTACCAATGACCAAA |
| TCAAAGAAATGACTCGCAAGGTTAGTGCTGAGGTTGACTTAGTTCATCA |
| GCAAACGCAGAATCAGCGGTATGCTCTTCTCATATTGGCGCTACTGCA |
| AAGGATATTTCTAATGTCGTCACTGATGCTGCTTCTGGTGTGGTTGATA |
| TTTTTCATGGTATTGATAAAGCTGTTGCCGATACTTGGAACAATTTCTG |
| GAAAGACGGTAAAGCTGATGTATTGGCTCTAATTTGTCTAGGAAATA |
| ACCGTCAGGATTGACACCCTCCCAATTGTATGTTTTCATGCCTCCAAAT |
| CTTGGAGGCTTTTTTATGGTTCGTTCTTATTACCCTTCTGAATGTCACGC |
| TGATTATTTTGACTTTGAGCGTATCGAGGCTCTTAAACCTGCTATTGAG |
| GCTTGTGGCATTTCTACTCTTTCTCAATCCCCAATGCTTGGCTTCCATAA |
| GCAGATGGATAACCGCATCAAGCTCTTGGAAGAGATTCTGTCTTTTCGT |
| ATGCAGGGCGTTGAGTTCGATAATGGTGATATGTATGTTGACGGCCATA |
| AGGCTGCTTCTGACGTTCGTGATGAGTTTGTATCTGTTACTGAGAAGTT |
| AATGGATGAAGCTTGGCACAATGCTACAATGTGCTCCCCCAACTTGATTT |
| AATAACACTATAGACCACCGCCCCGAAGGGGACGAAAATGGTTTTTA |
| GAGAACGAGAAGACGGTTACGCAGTTTTGCCGCAAGCTGGCTGCTGAA |
| CGCCCTCTTAAGGATATTCGCGATGAGTATAATTACCCCAAAAAGAAA |
| GGTATTAAGGATGAGTGTTCAAGATTGCTGGAGGCCTCCACTATGAA |
| TCGCGTAGAGGCTTTGCTATTCAGCGTTTGATGAATGCAATGCGACAGG |
| CTCATGCTGATGGTTGGTTTATCGTTTTTGACACTCTCACGTTGGCTGAC |
| GACCGATTAGAGGCGTTTTATGATAATCCCAATGCTTTGCGTGACTATT |
| TTCGTGATATTGGTCGTATGGTTCTTGCTGCCGAGGGTCGCAAGGCTAA |
| TGATTCACACGCCGACTGCTATCAGTATTTTTGTGTGCCTGAGTATGGT |
| ACAGCTAATGCCGTCTTCATTTCCATGCGGTGCACTTTATGCGGACAC |
| TTCCTACAGGTAGCGTTGACCCTAATTTTGGTCGTCGGGTACGCAATCG |
| CCGCCAGTTAAATAGCTTGCAAAATACGTGGCCTTATGGTTACAGTATG |
| CCCATCGCAGTTCGCTACACGCAGGACGCTTTTTCACGTTCTGGTTGGT |
| TGTGGCCTGTTGATGCTAAAGGTGAGCGCTTAAAGCTACCAGTTATAT |
| GGCTGTTGGTTTCTATGTGGCTAAATACGTTAACAAAAAGTCAGATATG |
| GACCTTGCTGCTAAAGGTCTAGGAGCTAAAGAATGGAACAACTCACTA |
| AAAACCAAGCTGTCGCTACTTCCCAAGAAGCTGTTCAGAATCAGAATG |
| AGCCGCAACTTCGGGATGAAATTGCTCACAATGACAAATCTGTCCACG |
| GAGTGCTTAATCCAACTTACCAAGCTGGGTTACGACGCGACGCCGTTCA |
| ACCAGATATTGAAGCAGAACGCAAAAAGAGAGATGAGATTGAGGCTG |
| GGAAAAGTTACTGTAGCCGACGTTTTGGCGGCGCAACCTGTGACGACA |
| AATCTGCTCAAATTTATGCGCGCTTCGATAAAAATGATTGGCGTATCCA |
| ACCTGCA |

| PhiX Genome Sequence |
| --- |
| SEQ ID NO: 1<br>Fragment #1<br>GAGTTTTATCGCTTCCATGACGCAGAAGTTAACACTTTCGGATATTTCT<br>GATGAGTCGAAAAATTATCTTGATAAAGCAGGAATTACTACTGCTTGTT<br>TACGAATTAAATCGAAGTGGACTGCTGGCGGAAAATGAGAAAATTCGA<br>CCTATCCTTGCGCAGCTCGAGAAGCTCTTACTTTGCGACCTTTCGCCAT<br>CAACTAACGATTCTGTCAAAAACTGACGCGTTGGATGAGGAGAAGTGG<br>CTTAATATGCTTGGCACGTTCGTCAAGGACTGGTTTAGATATGAGTCAC<br>atttttgttcatggtagagattctcttgttgacattttaaaagagcgtgg<br>ATTACTATCTGAGTCCGATGCTGTTCAACCACTAATAGGTAAGAAATCA<br>TGAGTCAAGTTACTGAACAATCCGTACGTTTCCAGACCGCTTTGGCCTC<br>TATTAAGCTCATTCAGGCTTCTGCCGTTTTGGATTTAACCGAAGATGAT<br>TTCGATTTTCTGACGAGTAACAAAGTTTGGATTGCTACTGACCGCTCTC<br>GTGCTCGTCGCTGCGTTGAGGCTTGCGTTTATGGTACGCTGGACTTTGT<br>GGGATACCCTCGCTTTCCTGCTCCTGTTGAGTTTATTGCTGCCGTCATTG<br>cttattatgttcatcccgtcaacattcaaacggcctgtctcatcatgga<br>AGGCGCTGAATTTACGGAAAACATTATTAATGGCGTCGAGCGTCCGGT<br>TAAAGCCGCTGAATTGTTCGCGTTTACCTTGCGTGTACGCGCAGGAAAC<br>ACTGACGTTCTTACTGACGCAGAAGAAAACGTGCGTCAAAAATTACGT<br>GCGGAAGGAGTGATGTAATGTCTAAAGGTAAAAAACGTTCTGGCGCTC<br>GCCCTGGTCGTCCGCAGCCGTTGCGAGGTACTAAAGGCAAGCGTAAAG<br>GCGCTCGTCTTTGGTATGTAGGTGGTCAACAATTTTAATTGCAGGGGCT<br>TCGGCCCCTTACTTGAGGATAAAATTATGTCTAATATTCAAACTGGCGCC<br>GAGCGTATGCCGCATGACCTTTCCCATCTTGGTTCCTTGCTGGTCAGA<br>TTGGTCGTCTTATTACCATTTCAACTACTCCGGTTATCGCTGGCGACTCC<br>TTCGAGATGGACGCCGTTGGCGCTCTCCGTCTTTCTCCATTGCGTCGTG<br>GCCTTGCTATTGACTCTACTGTAGACATTTTTACTTTTTATGTCCCTCAT<br>CGTCACGTTTATGGTGAACAGTGGATTAAGTTCATGAAGGATGGTGTTA<br>ATGCCACTCCTCTCCCGACTGTTAACACTACTGGTTATATTGACCATGC<br>CGCTTTTCTTGGCACGATTAACCCTGATACCAATAAAATCCCTAAGCAT<br>TTGTTTCAGGGTTATTTGAATATCTATAACA |
| SEQ ID NO: 2<br>Fragment #2<br>CCTAAGCATTTGTTTCAGGGTTATTTGAATATCTATAACAACTATTTTAA<br>AGCGCCGTGGATGCCTGACCGTACCGAGGCTAACCCTAATGAGCTTAA<br>TCAAGATGATGCTCGTTATGGTTTCCGTTGCTGCCATCTCAAAAACATT<br>TGGACTGCTCCGCTTCCTCCTGAGACTGAGCTTTCTCGCCAAATGACGA<br>CTTCTACCACATCTATTGACATTATGGGTCTGCAAGCTGCTTATGCTAA<br>TTTGCATACTGACCAAGAACGTGATTACTTCATGCAGCGTTACCATGAT<br>GTTATTTCTTCATTTGGAGGTAAAACCTCTTATGACGCTGACAACCGTC<br>CTTTACTTGTCATGCGCTCTAATCTCTGGGCATCTGCTATGATGTTGAT<br>GGAACTGACCAAACGTCGTTAGGCCAGTTTTCTGGTCGTGTTCAACAGA<br>CCTATAAACATTCTGTGCCGCGTTTCTTTGTTCCTGAGCATGGCACTATG<br>TTTACTCTTGCGCTTGTTCGTTTTCCGCCTACTGCGACTAAAGAGATTCA<br>GTACCTTAACGCTAAAGGTGCTTTGACTTATACCGATATTGCTGGCGAC<br>CCTGTTTTGTATGGCAACTTGCCGCCGCGTGAAATTTCTATGAAGGATG<br>TTTTCCGTTCTGGTGATTCGTCAAGAAGTTTAAGATTGCTGAGGGTCA<br>GTGGTATCGTTATGCGCCTTCGTATGTTTCTCCTGCTTATCACCTTCTTG<br>AAGGCTTCCCATTCATTCAGGAACCGCCTTCTGGTGATTTGCAAGAACG<br>CGTACTTATTCGCCACCATGATTATGACCAGTGTTTCCAGTCCGTTCAG<br>TTGTTGCAGTGGAATAGTCAGGTTAAATTTAATGTGACCGTTTATCGCA<br>ATCTGCCGACCACTCGCGATTCAATCATGACTTCGTGATAAAAGATTGA<br>GTGTGAGGTTATAACGCCGAAGCGGTAAAAATTTTAATTTTTGCCGCTG<br>AGGGGTTGACCAAGCGAAGCGCGGTAGGTTTTCTGCTTAGGAGTTTAA<br>TCATGTTTCAGACTTTTATTTCTCGCCATAATTCAAACTTTTTTTCTGAT<br>AAGCTGGTTCTCACTTCTGTTACTCCAGCTTCTTCGGCACCTGTTTTACA<br>GACACCTAAAGCTACATCGTCAACGTTATATTTTGATAGTTTGACGGTT<br>AATGCTGGTAATGGTGGTTTTCTTCATTGCATTCAGATGGATACATCTG<br>TCAACGCCGCTAATCAGGTTGTTTCTGTTGGTGCTGATATTGCTTTTGAT<br>GCCGACCCTAAATTTTTTGCCTGTTTGGTTCGCTTTGAGTCTTCTTCGGT<br>TCCGACTACCCTCCCGACTGCCTATGATGTTTATCCTTTGAATGGTCGCC<br>ATGATGGTGGTTATTATACC |
| SEQ ID NO: 3<br>Fragment #3<br>TTATCCTTTGAATGGTCGCCATGATGGTGGTTATTATACCGTCAAGGAC<br>TGTGTGACTATTGACGTCCTTCCCCGTACGCCGGGCAATAACGTTTATG<br>TTGGTTTCATGGTTTGGTCTAACTTTACCGCTACTAAATGCCGCGGATT<br>GGTTTCGCTGAATCAGGTTATTAAAGAGATTATTTGTCTCCAGCCACTT<br>AAGTGAGGTGATTTATGTTTGGTGCTATTGCTGGCGGTATTGCTTCTGC<br>TCTTGCTGGTGGCGCCATGTCTAAATTGTTTGGAGGCGGTCAAAAAGCC<br>GCCTCCGGTGGCATTCAAGGTGATGTGCTTGCTACCGATAACAATACTG<br>TAGGCATGGGTGATGCTGGTATTAAATCTGCCATTCAAGGCTCTAATGT<br>TCCTAACCCTGATGAGGCCGCCCCTAGTTTTGTTTCTGGTGCTATGGCT<br>AAAGCTGGTAAAGGACTTCTTGAAGGTACGTTGCAGGCTGGCACTTCT<br>GCCGTTTCTGATAAGTTGCTTGATTTGGTTGGACTTGGTGGCAAGTCTG<br>CCGCTGATAAAGGAAAGGATACTCGTGATTATCTTGCTGCTGCATTTCC |
| TGAGCTTAATGCTTGGGAGCGTGCTGGTGCTGATGCTTCCTCTGCTGGT<br>ATGGTTGACGCCGGATTTGAGAATCAAAAAGAGCTTACTAAAATGCAA<br>CTGGACAATCAGAAAGAGATTGCCGAGATGCAAAATGAGACTCAAAA<br>AGAGATTGCTGGCATTCAGTCGGCGACTTCACGCCAGAATACGAAAGA<br>CCAGGTATATGCACAAAATGAGATGCTTGCTTATCAACAGAAGGAGTC<br>TACTGCTCGCGTTGCGTCTATTATGGAAAACACCAATCTTTCCAAGCAA<br>CAGCAGGTTTCCGAGATTATGCGCCAAATGCTTACTCAAGCTCAAACG<br>GCTGGTCAGTATTTTACCAATGACCAAATCAAAGAAATGACTCGCAAG<br>GTTAGTGCTGAGGTTGACTTAGTTCATCAGCAAACGCAGAATCAGCGG<br>TATGGCTCTTCTCATATTGGCGCTACTGCAAAGGATATTTCTAATGTCG<br>TCACTGATGCTGCTTCTGGTGTGGTTGATATTTTTCATGGTATTGATAAA<br>GCTGTTGCCGATACTTGGAACAATTTCTGGAAAGACGGTAAAGCTGAT<br>GGTATTGGCTCTAATTTGTCTAGGAAATAACCGTCAGGATTGACACCCT<br>CCCAATTGTATGTTTTCATGCCTCCAAATCTTGGAGGCTTTTTTATGGTT<br>CGTTCTTATTACCCTTCTGAATGTCACGCTGATTATTTTGACTTTGAGCG<br>TATCGAGGCTCTTAAACCTGCTATTGAGGCTTGTGGCATTTCTACTCTTT<br>CTCAATCCCCAATGCTTGGCTTCCATAAGCAGAT |
| SEQ ID NO: 4<br>Fragment #4<br>CTCTTTCTCAATCCCCAATGCTTGGCTTCCATAAGCAGATGGATAACCG<br>CATCAAGCTCTTGGAAGAGATTCTGTCTTTTCGTATGCAGGGCGTTGAG<br>TTCGATAATGGTGATATGTATGTTGACGGCCATAAGGCTGCTTCTGACG<br>TTCGTGATGAGTTTGTATCTGTTACTGAGAAGTTAATGGATGAATTGGC<br>ACAATGCTACAATGTGCTCCCCCAACTTGATATTAATAACACTATAGAC<br>CACCGCCCGAAGGGGACGAAAAATGGTTTTTAGAGAACGAGAAGAC<br>GGTTACGCAGTTTTGCCGCAAGCTGGCTGCTGAACGCCCTCTTAAGGAT<br>ATTCGCGATGAGTATAATTACCCCAAAAAGAAAGGTATTAAGGATGAG<br>TGTTCAAGATTGCTGGAGGCCTCCACTATGAAATCGCGTAGAGGCTTTG<br>CTATTCAGCGTTTGATGAATGCAATGCGACAGGCTCATGCTGATGGTTG<br>GTTTATCGTTTTTGACACTCTCACGTTGGCTGACGACCGATTAGAGGCG<br>TTTTATGATAATCCCAATGCTTTGCGTGACTATTTTCGTGATATTGGTCG<br>TATGGTTCTTGCTGCCGAGGGTCGCAAGGCTAATGATTCACACGCCGAC<br>TGCTATCAGTATTTTTGTGTGCCTGAGTATGGTACAGCTAATGGCCGTC<br>TTCATTTCCATGCGGTGCACTTTATGCGGACACTTCCTACAGGTAGCGT<br>TGACCCTAATTTTGGTCGTCGGGTACGCAATCGCCGCCAGTTAAATAGC<br>TTGCAAAATACGTGGCCTTATGGTTACAGTATGCCCATCGCAGTTCGCT<br>ACACGCAGGACGCTTTTTCACGTTCTGGTTGGTTGTGGCCTGTTGATGC<br>TAAAGGTGAGCCGCTTAAAGCTACCAGTTATATGGCTGTTGGTTTCTAT<br>GTGGCTAAATACGTTAACAAAAAGTCAGATATGGACCTTGCTGCTAAA<br>GGTCTAGGAGCTAAAGAATGGAACAACTCACTAAAAACCAAGCTGTCG<br>CTACTTCCCAAGAAGCTGTTCAGAATCAGAATGAGCCGCAACTTCGGG<br>ATGAAAATGCTCACAATGACAAATCTGTCCACGGAGTGCTTAATCCAA<br>CTTACCAAGCTGGGTTACGACGCGACGCCGTTCAACCAGATATTGAAG<br>CAGAACGCAAAAAGAGAGATGAGATTGAGGCTGGGAAAAGTTACTGT<br>AGCCGACGTTTTGGCGGCGCAACCTGTGACGACAAATCTGCTCAAATTT<br>ATGCGCGCTTCGATAAAAATGATTGGCGTATCCAACCTGCAGAGTTTTA<br>TCGCTTCCATGACGCAGAAGTTAACACTTTCG |

Example 4

Synthesis of a Functional DNA Molecule and Protein Moiety

The nucleic acid sequence encoding a functional green fluorescent protein (GFP) and appropriate regulatory sequences for expression is entered into ARCHETYPE® (Synthetic Genomics, Inc., San Diego, Calif.) or another software that divides the sequence into about 60 bp oligonucleotides with about 30 bp overlaps. The first and last oligonucleotides contain primer binding domains for PCR amplification and NotI restriction sites to release the primer binding domains following amplification and expose overlapping regions for DNA assembly, if necessary to assemble larger fragments.

The system includes a BIOMEK® NXP, Span-8 laboratory automation workstation (Beckman Instruments Inc., Fullerton, Calif.) with integrated thermal-cycling capabilities as one sub-unit. Additional sub-units include an automated in vitro translation system containing vessels with reagents for carrying out a cell-free translation of nucleic acid into protein. Following entry into the transmitting unit the biological sequence information is transmitted to a receiving unit located in a laboratory in a remote city.

Oligonucleotide Synthesis

Following a synthesis plan similar to those described above the biological sequence information is received by a receiving unit of the invention, as described in the Examples. In this embodiment the receiving unit is a computer connected to the same computer network as the transmitting unit. The receiving unit is connected to an assembly unit, which in this embodiment has a BIOAUTOMATION™ 192E oligonucleotide synthesizer (BioAutomation Corp., Plano, Tex.) as one sub-unit. The additional sub-units of the assembly unit, including the sub-unit for in vitro translation, are all set up prior to receiving the biological sequence information by charging all vessels with requisite chemicals, reagents, and biological building blocks, as well as preparing all software programming prior to receiving the biological sequence information so that activation of the synthesis of the biological entity can begin immediately upon receiving the sequence information.

After receipt of the biological sequence information software within the assembly unit directs the synthesis of the oligonucleotides, which are synthesized using dNTPs or phosphoramidites and other reagents previously provided to the system. This step is done in the same manner as described above in the Examples and the set of oligonucleotides are produced, which are then assembled and amplified as described in the Examples to produce the nucleic acid sequence encoding the GFP gene with appropriate regulatory sequences necessary for expression.

In vitro and automated transcription and translation can be performed on the assembled nucleic acid sequence in a distinct reaction zone of the reaction container prepared for that purpose. Various kits are commercially available for performing in vitro translation and/or cell-free protein expression and can be conveniently employed in the present invention, e.g., PIERCE® (Pierce Biotechnology Inc., Rockford, Ill.) In Vitro Protein Expression Systems available from THERMO SCIENTIFIC® (Thermo Fisher Scientific, Inc., Waltham, Mass.) or the T7 RiboMAX™ Express kit from PROMEGA® (Promega Corp, Madison, Wis.), which can generate 27 kb in vitro transcripts in minutes. Different kits are available depending on the type and size of protein to be translated. The reaction zone of the reaction container where the reaction is to be performed is pre-charged with all necessary reagents. The GFP construct was also designed to contain a T7 or a strong *E. coli* promoter upstream of the coding sequence, a ribosome binding site with a spacing sequence of 5-7 bp upstream of the AUG translational start point and an untranslated region downstream of the stop coding.

The synthetic PCR product is added to the protein expression components in the designated reaction zone. Following the expression reaction, a black light is held to the reaction mixture and the presence of translated GFP is confirmed by the emission of green light.

Example 5

Synthesis of an Antigenic Biological Product

HER-2 (human epidermal growth factor receptor 2) is a protein for which amplification or over-expression play a role in the progression of certain breast cancers. The protein is encoded by the ERBB2 gene. A number of antibody therapies are available that target HER-2. A vaccine can be made containing the HER-2 antigen, which can be administered to a patient who will then form an antigenic response to the vaccine and produce antibodies to HER-2. The vaccine can be useful in cancer treatments, and in any therapy where the production of HER-2 antibodies finds useful application.

The sequence of HER-2 protein is entered into a software program that divides the sequence into an appropriate number of overlapping fragments representing sub-assemblies of the gene. Suitable regulatory sequences are included in the sequence. Each fragment is of appropriate length for gene synthesis and is designed to overlap the next fragment by an appropriate number of base pairs such as, for example, about 40 bp. The biological sequence information is transmitted by a transmitting unit to a receiving unit of a system of the invention. As explained herein the gene can be assembled as a series of overlapping oligonucleotides, and a sub-unit of the assembly unit assembles the oligonucleotides into the final dsDNA molecule, or the dsDNA molecule can be assembled in a different zone of the reaction container. Suitable regulatory sequences for expression are included. The assembled gene is transferred to another sub-unit of the assembly unit or to another zone of the reaction container and cell-free, in vitro transcription is performed, and then to another sub-unit or another zone for translation of the DNA sequence, as explained herein. A purification step is performed if desired. The harvested HER-2 may be formulated and is utilized as an antigenic vaccine.

Example 6

Synthesis of a DNA Vaccine

The invention also finds use in the production of a DNA vaccine. The DNA sequence encoding for one or more HIV proteins is entered into a software program that separates the DNA sequence into overlapping oligonucleotide fragments of appropriate length, including DNA sequences of an appropriate plasmid (e.g., pGA2/JS2) with appropriate regulatory sequences for expression.

The sequence is transmitted by a transmitting unit of the invention to a receiving unit of a system of the invention. As described herein, the receiving unit provides the sequence to an assembly unit of the invention and the assembly unit begins synthesis of overlapping oligonucleotides, which will be assembled by a subunit of the assembly unit (or by the same sub-unit in a different zone of the reaction container) into the full plasmid vaccine. DNA may then be formulated and used as a DNA vaccine. When injected into the patient the DNA vaccine will provide instructions to cells to make one or more HIV proteins, which will then provoke an immune response. The technique is applicable to any DNA virus that can be incorporated into a plasmid or other vector that can be injected into the patient to be treated to provide immunity.

West Nile virus is another example of a pathogen that is susceptible to prevention through the use of a DNA vaccine using the prM and E genes.

Example 7

Synthesis of a Vaccine from Protein Sub-Units

Sub-unit vaccines offer an opportunity to present an antigen to the immune system without the need to introduce whole viral particles. One example is the OPTAFLU® (Novartis Vaccines and Diagnostics, GmbH, Marburg, Germany) vaccine for providing immunity to the influenza virus. The present invention can be applied in the rapid production of sub-unit vaccines.

The A/H3N2, A/H1N1 and B strains of the current flu virus are obtained from the World Health Organization strain recommendations and are used in the preparation of a trivalent vaccine using the viral surface antigens. The nucleic acid sequences are separated into fragments as described above using an appropriate software program, with appropriate regulatory sequences included. After synthesis of the nucleic acid, as described above, the nucleic acid is transferred to a sub-unit of the assembly unit (or to another zone of the reaction container) for in vitro translation. The vaccine can be produced in a sub-unit where a cell culture is being maintained, which sub-unit has been previously prepared with an established culture of MDCK cells (a canine kidney cell line) in appropriate media.

Example 8

Synthesis of a Virus-Like Particle Vaccine

Non-infectious virus-like particles (VLPs) can be used to manufacture a vaccine with the capacity to activate the immune system without the need to present an assembled viral particle. A vaccine against human papilloma virus (HPV) can be manufactured using the L1 and/or L2 major capsid proteins, which self-assemble into virus-like particles that are effective as antigens. These VLPs can be assembled in yeast, insect cells, mammalian cells, or bacteria. An example of this type of vaccine is GARDASIL® (Merck Sharp & Dohme Corp., Whitehouse Station, N.J.). Multiple HPV L1 virus-like particles can be included in a single vaccine for the broadest spectrum of immunity.

VLPs of a combination of HPV types selected from types 6, 11, 16, 18, 31, 35, 45, 52, and 58 are selected. The VLPs can be of L1 or L1+L2 protein. The nucleic acid sequences coding for these proteins are identified and separated into fragments as described above using an appropriate software with appropriate regulatory sequences for expression in the chosen cell type included. The nucleic acid sequence information is then transmitted by a transmitting unit to a receiving unit of the invention located in a remote location. The receiving unit provides the sequence information to the assembly unit of the system, and the VLPs are synthesized. As described above, the DNA molecule can be assembled from overlapping oligonucleotide fragments into one or more whole dsDNA molecules.

After synthesis, as described above, the DNA is transferred to a sub-unit of the assembly unit (or to another zone of the reaction container) for in vitro translation in an established cell culture being maintained on the system. The vaccine is produced by the cells in that sub-unit. The translated proteins are provided to another sub-unit of the system where they are pooled and self-assemble into VLPs that are useful as a vaccine against HPV.

Example 9

Synthesis of a Complete Viral Vaccine

In another embodiment a whole virus vaccine can be synthesized in cell culture using a reverse genetics technique. The influenza A genome is composed of eight viral gene segments, including the HA and NA segments, which are important in immune response to the virus. In one embodiment the assembly unit has a subunit maintaining, for example, MDCK cells, 293T cells, or Vero cells for virus production (these components can also be maintained in one or more additional zones of the reaction container). Plasmids containing multiple transcription cassettes can be constructed containing the eight viral genes and necessary regulatory sequences. The eight genes can be present on multiple plasmids or a single plasmid if desired. The HA and NA segments are based upon sequences derived from a virus that is presenting a local threat. Thus, in one embodiment the six non-varying genes are prepared ahead of time and only the HA and NA genes are synthesized by the system. The six non-varying genes can then be treated as reagents in the method. But in another embodiment a subunit of the assembly unit synthesizes the plasmids based upon information received from the receiving unit. In either embodiment, after synthesis the plasmids are transfected into the cell culture being maintained in another subunit of the assembly unit under conditions for high transfection efficiency. The transfected cells produce whole virus particles which can be formulated as a live, attenuated vaccine, or as a killed or further inactivated vaccine, as desired.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are within the following claims.

What is claimed is:

1. An automated system for the synthesis of a double-stranded DNA molecule according to provided biological sequence information, comprising:

an assembly unit that assembles the double-stranded DNA molecule according to the provided biological sequence information, the assembly unit comprising or connected to vessels containing a plurality of oligonucleotide molecules and containing components that transport reagents within the system and that executes steps in an automated method for synthesizing the double-stranded DNA molecule, wherein the method comprises the assembly of one or more dsDNA molecule(s) by joining the plurality of oligonucleotides, and wherein no human intervention occurs after the method is initiated and until the double-stranded DNA molecule is synthesized; and the system further comprising a non-transitory computer readable medium containing software programming instructions that direct steps in the assembly unit for the assembly of the plurality of oligonucleotide molecules into the double stranded DNA molecule in the automated method, wherein the software programming instructions direct a step of PCR amplification in a first reaction zone of a reaction container, a step of error correction in a second reaction zone of a reaction container performed after the step of PCR amplification, a step of DNA assembly in a third reaction zone of a reaction container, and directs the transport of reagents from one reaction zone to the next, wherein the reaction container is a reaction plate, and the reaction zones comprise one or more reaction wells on the reaction plate; and wherein the system further comprises a robotic arm configured to transfer the oligonucleotide molecules from the first reaction zone to the second reaction zone, and from the second reaction zone to the third reaction zone, the oligonucleotide molecules successively accumulating in each reaction zone.

2. The automated system of claim 1 wherein the oligonucleotides are provided to a sub-unit of the assembly unit for amplification of the oligonucleotides by the step of PCR.

3. The automated system of claim 1 wherein the oligonucleotides are from 40-100 nucleotides in length.

4. The automated system of claim 1 wherein the system further comprises software programming instructions and reagents directing steps for the transcription of the DNA molecule into an RNA molecule.

5. The automated system of claim 4 wherein the system further comprises software programming instructions and reagents directing translation of the RNA molecule into a protein molecule.

6. The system of claim 5 wherein the protein is further processed by the system to produce a virus particle or a portion of a virus particle.

7. The system of claim 6 wherein the virus particle or portion of a virus particle comprises a protein antigen.

8. The system of claim 1 wherein the assembly unit further comprises or is connected to a vessel comprising a host cell.

9. The system of claim 1 wherein the conditions for a step are established in a reaction zone and a sample is subsequently moved into the reaction zone.

10. The system of claim 1 further comprising that the software programming instructions direct an RNA transcription step performed in a reaction zone of a reaction container.

11. The system of claim 1 wherein the reaction container is a 96 well plate having dimensions of about 127 mm×about 85 mm.

12. The automated system of claim 1 wherein the double stranded DNA molecule is greater than 500 bp in size.

13. The automated system of claim 1 wherein the software programming instructions comprise instructions for simultaneously assembling the plurality of oligonucleotide molecules into the dsDNA molecule(s).

14. The automated system of claim 2 wherein the assembly unit further comprises or is connected to vessels containing a nucleic acid molecule selected from the group consisting of: a plasmid, a vector, a regulatory sequence, a promoter sequence, a binding element for a trans-acting factor, and a signal sequence.

15. The automated system of claim 1 wherein the plurality of oligonucleotide molecules are 30-110 nucleotides in length.

16. The automated system of claim 1 wherein the overlapping oligonucleotides are assembled in an isothermal reaction.

17. The automated system of claim 1 wherein the plurality of oligonucleotide molecules is assembled into the dsDNA molecule(s) in a simultaneous reaction.

18. The automated system of claim 1 wherein the overlapping oligonucleotides are assembled in a reaction using an exonuclease and a DNA polymerase.

19. The automated system of claim 1 wherein the double stranded DNA molecule is greater than 500 bp in size.

20. The automated system of claim 1 wherein the error correction reaction comprises the use of a mismatch endonuclease.

21. The automated system of claim 20 wherein the error correction reaction further comprises the use of exonuclease III.

22. The automated system of claim 1 comprising a single reaction container.

23. The automated system of claim 22 wherein the reaction container is a 96 well plate.

* * * * *

SEQUENCE LISTING

```
<160> NUMBER OF SEQ ID NOS: 6

<210> SEQ ID NO 1
<211> LENGTH: 1400
```

```
<212> TYPE: DNA
<213> ORGANISM: phi X virus

<400> SEQUENCE: 1
gagttttatc gcttccatga cgcagaagtt aacactttcg atatttctg atgagtcgaa      60
aaattatctt gataaagcag gaattactac tgcttgttta cgaattaaat cgaagtggac    120
tgctggcgga aaatgagaaa attcgaccta tccttgcgca gctcgagaag ctcttacttt    180
gcgacctttc gccatcaact aacgattctg tcaaaaactg acgcgttgga tgaggagaag    240
tggcttaata tgcttggcac gttcgtcaag gactggttta gatatgagtc acattttgtt    300
catggtagag attctcttgt tgacatttta aaagagcgtg gattactatc tgagtccgat    360
gctgttcaac cactaatagg taagaaatca tgagtcaagt tactgaacaa tccgtacgtt    420
tccagaccgc tttggcctct attaagctca ttcaggcttc tgccgttttg gatttaaccg    480
aagatgattt cgattttctg acgagtaaca agtttggat tgctactgac cgctctcgtg    540
ctcgtcgctg cgttgaggct tgcgtttatg gtacgctgga cttgtgggga taccctcgct    600
ttcctgctcc tgttgagttt attgctgccg tcattgctta ttatgttcat cccgtcaaca    660
ttcaaacggc ctgtctcatc atggaaggcg ctgaatttac ggaaaacatt attaatggcg    720
tcgagcgtcc ggttaaagcc gctgaattgt tcgcgtttac cttgcgtgta cgcgcaggaa    780
acactgacgt tcttactgac gcagaagaaa acgtgcgtca aaaattacgt gcggaaggag    840
tgatgtaatg tctaaaggta aaaaacgttc tggcgctcgc cctggtcgtc cgcagccgtt    900
gcgaggtact aaaggcaagc gtaaaggcgc tcgtctttgg tatgtaggtg gtcaacaatt    960
ttaattgcag gggcttcggc cccttacttg aggataaatt atgtctaata ttcaaactgg   1020
cgccgagcgt atgccgcatg accttttccca tcttggcttc cttgctggtc agattggtcg   1080
tcttattacc atttcaacta ctccggttat cgctggcgac tccttcgaga tggacgccgt   1140
tggcgctctc cgtctttctc cattgcgtcg tggccttgct attgactcta ctgtagacat   1200
ttttactttt tatgtccctc atcgtcacgt ttatggtgaa cagtggatta agttcatgaa   1260
ggatggtgtt aatgccactc ctctcccgac tgttaacact actggttata ttgaccatgc   1320
cgcttttctt ggcacgatta accctgatac caataaaatc cctaagcatt tgtttcaggg   1380
ttatttgaat atctataaca                                                1400

<210> SEQ ID NO 2
<211> LENGTH: 1400
<212> TYPE: DNA
<213> ORGANISM: phi X virus

<400> SEQUENCE: 2
cctaagcatt tgtttcaggg ttatttgaat atctataaca actatttaa agcgccgtgg      60
atgcctgacc gtaccgaggc taacccctaat gagcttaatc aagatgatgc tcgttatggt    120
ttccgttgct gccatctcaa aaacatttgg actgctccgc ttcctcctga gactgagctt    180
tctcgccaaa tgacgacttc taccacatct attgacatta tgggtctgca agctgcttat    240
gctaatttgc atactgacca agaacgtgat tacttcatgc agcgttacca tgatgttatt    300
tcttcatttg gaggtaaaac ctcttatgac gctgacaacc gtcctttact tgtcatgcgc    360
tctaatctct gggcatctgg ctatgatgtt gatggaactg accaaacgtc gttaggccag    420
ttttctggtc gtgttcaaca gacctataaa cattctgtgc cgcgtttctt tgttcctgag    480
catggcacta tgtttactct tgcgcttgtt cgttttccgc ctactgcgac taaagagatt    540
```

```
cagtaccta acgctaaagg tgctttgact tataccgata ttgctggcga ccctgttttg       600
tatggcaact tgccgccgcg tgaaatttct atgaaggatg ttttccgttc tggtgattcg       660
tctaagaagt ttaagattgc tgagggtcag tggtatcgtt atgcgccttc gtatgtttct       720
cctgcttatc accttcttga aggcttccca ttcattcagg aaccgccttc tggtgatttg       780
caagaacgcg tacttattcg ccaccatgat tatgaccagt gtttccagtc cgttcagttg       840
ttgcagtgga atagtcaggt taaatttaat gtgaccgttt atcgcaatct gccgaccact       900
cgcgattcaa tcatgacttc gtgataaaag attgagtgtg aggttataac gccgaagcgg       960
taaaaatttt aattttttgcc gctgaggggg tgaccaagcg aagcgcggta ggttttctgc      1020
ttaggagttt aatcatgttt cagactttta tttctcgcca taattcaaac ttttttttctg      1080 ataagctggt tctcacttct gttactccag cttcttcggc acctgtttta cagacaccta      1140
aagctacatc gtcaacgtta tattttgata gtttgacggt taatgctggt aatggtggtt      1200
ttcttcattg cattcagatg gatacatctg tcaacgccgc taatcaggtt gtttctgttg      1260
gtgctgatat tgcttttgat gccgacccta aattttttgc ctgtttggtt cgctttgagt      1320
cttcttcggt tccgactacc ctcccgactg cctatgatgt ttatcctttg aatggtcgcc      1380
atgatggtgg ttattatacc                                                  1400

<210> SEQ ID NO 3
<211> LENGTH: 1400
<212> TYPE: DNA
<213> ORGANISM: phi X virus

<400> SEQUENCE: 3
ttatcctttg aatggtcgcc atgatggtgg ttattatacc gtcaaggact gtgtgactat        60
tgacgtcctt ccccgtacgc cgggcaataa cgtttatgtt ggtttcatgg tttggtctaa       120
ctttaccgct actaaatgcc gcggattggt ttcgctgaat caggttatta aagagattat       180
ttgtctccag ccacttaagt gaggtgattt atgtttggtg ctattgctgg cggtattgct       240
tctgctcttg ctggtggcgc catgtctaaa ttgtttggag gcggtcaaaa agccgcctcc       300
ggtggcattc aaggtgatgt gcttgctacc gataacaata ctgtaggcat gggtgatgct       360
ggtattaaat ctgccattca aggctctaat gttcctaacc ctgatgaggc cgcccctagt       420
tttgtttctg gtgctatggc taaagctggt aaaggacttc ttgaaggtac gttgcaggct       480
ggcacttctg ccgtttctga taagttgctt gatttggttg gacttggtgg caagtctgcc       540
gctgataaag gaaaggatac tcgtgattat cttgctgctg catttcctga gcttaatgct       600
tgggagcgtg ctggtgctga tgcttcctct gctggtatgg ttgacgccgg atttgagaat       660
caaaaagagc ttactaaaat gcaactggac aatcagaaag agattgccga tgcaaaat       720 gagactcaaa aagagattgc tggcattcag tcggcgactt cacgccagaa tacgaaagac      780
caggtatatg cacaaaatga tgcttgct atcaacaga aggagtctac tgctcgcgtt       840
gcgtctatta tggaaaacac caatctttcc aagcaacagc aggtttccga gattatgcgc       900
caaatgctta ctcaagctca aacggctggt cagtatttta ccaatgacca aatcaaagaa       960
atgactcgca aggttagtgc tgaggttgac ttagttcatc agcaaacgca gaatcagcgg      1020
tatggctctt ctcatattgg cgctactgca aggatatt ctaatgtcgt cactgatgct      1080
gcttctggtg tggttgatat ttttcatggt attgataaag ctgttgccga tacttggaac      1140
aatttctgga aagacggtaa agctgatggt attggctcta atttgtctag gaaataaccg      1200
tcaggattga caccctccca attgtatgtt ttcatgcctc caaatcttgg aggcttttt      1260
```

```
atggttcgtt cttattaccc ttctgaatgt cacgctgatt attttgactt tgagcgtatc      1320
gaggctctta aacctgctat tgaggcttgt ggcatttcta ctctttctca atccccaatg      1380
cttggcttcc ataagcagat                                                 1400
```

<210> SEQ ID NO 4
<211> LENGTH: 1346
<212> TYPE: DNA
<213> ORGANISM: phi X virus

<400> SEQUENCE: 4

```
ctctttctca atccccaatg cttggcttcc ataagcagat ggataaccgc atcaagctct       60
tggaagagat tctgtctttt cgtatgcagg gcgttgagtt cgataatggt gatatgtatg      120
ttgacggcca taaggctgct tctgacgttc gtgatgagtt tgtatctgtt actgagaagt      180
taatggatga attggcacaa tgctacaatg tgctccccca acttgatatt aataacacta      240
tagaccaccg ccccgaaggg gacgaaaaat ggtttttaga gaacgagaag acggttacgc      300
agttttgccg caagctggct gctgaacgcc ctcttaagga tattcgcgat gagtataatt      360
accccaaaaa gaaaggtatt aaggatgagt gttcaagatt gctggaggcc tccactatga      420
aatcgcgtag aggctttgct attcagcgtt tgatgaatgc aatgcgacag gctcatgctg      480
atggttggtt tatcgttttt gacactctca cgttggctga cgaccgatta gaggcgtttt      540
atgataatcc caatgctttg cgtgactatt tcgtgatatt ggtcgtatg gttcttgctg      600 ccgagggtcg caaggctaat gattcacacg ccgactgcta tcagtatttt tgtgtgcctg      660
agtatggtac agctaatggc cgtcttcatt tccatgcggt gcactttatg cggacacttc      720
ctacaggtag cgttgaccct aattttggtc gtcgggtacg caatcgccgc cagttaaata      780
gcttgcaaaa tacgtggcct tatggttaca gtatgcccat cgcagttcgc tacacgcagg      840
acgctttttc acgttctggt tggttgtggc ctgttgatgc taaaggtgag ccgcttaaag      900
ctaccagtta tatggctgtt ggtttctatg tggctaaata cgttaacaaa aagtcagata      960
tggaccttgc tgctaaaggt ctaggagcta agaatggaa caactcacta aaaaccaagc     1020
tgtcgctact tcccaagaag ctgttcagaa tcagaatgag ccgcaacttc gggatgaaaa     1080
tgctcacaat gacaaatctg tccacggagt gcttaatcca acttaccaag ctgggttacg     1140
acgcgacgcc gttcaaccag atattgaagc agaacgcaaa aagagagatg agattgaggc     1200
tgggaaaagt tactgtagcc gacgttttgg cggcgcaacc tgtgacgaca atctgctca      1260 aatttatgcg cgcttcgata aaaatgattg gcgtatccaa cctgcagagt tttatcgctt     1320
ccatgacgca gaagttaaca ctttcg                                         1346
```

<210> SEQ ID NO 5
<211> LENGTH: 5386
<212> TYPE: DNA
<213> ORGANISM: phi X virus

<400> SEQUENCE: 5

```
gagttttatc gcttccatga cgcagaagtt aacactttcg atatttctg atgagtcgaa       60 aaattatctt gataaagcag gaattactac tgcttgttta cgaattaaat cgaagtggac      120
tgctggcgga aaatgagaaa attcgaccta tccttgcgca gctcgagaag ctcttacttt      180
gcgacctttc gccatcaact aacgattctg tcaaaaactg acgcgttgga tgaggagaag      240
tggcttaata tgcttggcac gttcgtcaag gactggttta gatatgagtc acattttgtt      300
```

```
catggtagag attctcttgt tgacatttta aaagagcgtg gattactatc tgagtccgat      360
gctgttcaac cactaatagg taagaaatca tgagtcaagt tactgaacaa tccgtacgtt      420
tccagaccgc tttggcctct attaagctca ttcaggcttc tgccgttttg gatttaaccg      480
aagatgattt cgattttctg acgagtaaca aagtttggat tgctactgac cgctctcgtg      540
ctcgtcgctg cgttgaggct tgcgtttatg gtacgctgga ctttgtggga taccctcgct      600
ttcctgctcc tgttgagttt attgctgccg tcattgctta ttatgttcat cccgtcaaca      660
ttcaaacggc ctgtctcatc atggaaggcg ctgaatttac ggaaaacatt attaatggcg      720
tcgagcgtcc ggttaaagcc gctgaattgt tcgcgtttac cttgcgtgta cgcgcaggaa      780
acactgacgt tcttactgac gcagaagaaa acgtgcgtca aaaattacgt gcggaaggag      840
tgatgtaatg tctaaaggta aaaacgttc tggcgctcgc cctggtcgtc cgcagccgtt      900
gcgaggtact aaaggcaagc gtaaaggcgc tcgtctttgg tatgtaggtg gtcaacaatt      960
ttaattgcag gggcttcggc cccttacttg aggataaatt atgtctaata ttcaaactgg     1020
cgccgagcgt atgccgcatg ccttttccca tcttggcttc cttgctggtc agattggtcg     1080
tcttattacc atttcaacta ctccggttat cgctggcgac tccttcgaga tggacgccgt     1140
tggcgctctc cgtctttctc cattgcgtcg tggccttgct attgactcta ctgtagacat     1200
tttacttttt tatgtccctc atcgtcacgt ttatggtgaa cagtggatta agttcatgaa     1260
ggatggtgtt aatgccactc ctctcccgac tgttaacact actggttata ttgaccatgc     1320
cgcttttctt ggcacgatta accctgatac caataaaatc cctaagcatt gtttcaggg      1380 ttatttgaat atctataaca actattttaa agcgccgtgg atgcctgacc gtaccgaggc     1440
taaccctaat gagcttaatc aagatgatgc tcgttatggt ttccgttgct gccatctcaa     1500
aaacatttgg actgctccgc ttcctcctga gactgagctt tctcgccaaa tgacgacttc     1560
taccacatct attgacatta tgggtctgca agctgcttat gctaatttgc atactgacca     1620
agaacgtgat tacttcatgc agcgttacca tgatgttatt tcttcatttg gaggtaaaac     1680
ctcttatgac gctgacaacc gtcctttact tgtcatgcgc tctaatctct gggcatctgg     1740
ctatgatgtt gatggaactg accaaacgtc gttaggccag ttttctggtc gtgttcaaca     1800
gacctataaa cattctgtgc cgcgtttctt tgttcctgag catggcacta tgtttactct     1860
tgcgcttgtt cgttttccgc ctactgcgac taaagagatt cagtacctta cgctaaagg      1920 tgctttgact tataccgata ttgctggcga ccctgttttg tatggcaact gccgccgcg      1980 tgaaatttct atgaaggatg ttttccgttc tggtgattcg tctaagaagt ttaagattgc     2040
tgagggtcag tggtatcgtt atgcgccttc gtatgtttct cctgcttatc accttcttga     2100
aggcttccca ttcattcagg aaccgccttc tggtgatttg caagaacgcg tacttattcg     2160
ccaccatgat tatgaccagt gtttccagtc cgttcagttg ttgcagtgga atagtcaggt     2220
taaatttaat gtgaccgttt atcgcaatct gccgaccact cgcgattcaa tcatgacttc     2280
gtgataaaag attgagtgtg aggttataac gccgaagcgg taaaaatttt aattttttgcc    2340 gctgagggt tgaccaagcg aagcgcggta ggttttctgc ttaggagttt aatcatgttt      2400 cagacttta tttctcgcca taattcaaac tttttttctg ataagctggt tctcacttct      2460
gttactccag cttcttcggc acctgttta cagacaccta aagctacatc gtcaacgtta     2520
tattttgata gtttgacggt taatgctggt aatggtggtt tcttcattg cattcagatg     2580 gatacatctg tcaacgccgc taatcaggtt gtttctgttg gtgctgatat tgctttgat      2640 gccgacccta aatttttgc ctgtttggtt cgctttgagt cttcttcggt tccgactacc      2700
```

```
ctcccgactg cctatgatgt ttatcctttg aatggtcgcc atgatggtgg ttattatacc    2760
gtcaaggact gtgtgactat tgacgtcctt ccccgtacgc cgggcaataa cgtttatgtt    2820
ggtttcatgg tttggtctaa ctttaccgct actaaatgcc gcggattggt ttcgctgaat    2880
caggttatta aagagattat ttgtctccag ccacttaagt gaggtgattt atgtttggtg    2940
ctattgctgg cggtattgct tctgctcttg ctggtggcgc catgtctaaa ttgtttggag    3000
gcggtcaaaa agccgcctcc ggtggcattc aaggtgatgt gcttgctacc gataacaata    3060
ctgtaggcat gggtgatgct ggtattaaat ctgccattca aggtctaat gttcctaacc     3120 ctgatgaggc cgcccctagt tttgtttctg gtgctatggc taaagctggt aaaggacttc    3180
ttgaaggtac gttgcaggct ggcacttctg ccgtttctga taagttgctt gatttggttg    3240
gacttggtgg caagtctgcc gctgataaag gaaaggatac tcgtgattat cttgctgctg    3300
catttcctga gcttaatgct tgggagcgtg ctggtgctga tgcttcctct gctggtatgg    3360
ttgacgccgg atttgagaat caaaaagagc ttactaaaat gcaactggac aatcagaaag    3420
agattgccga gatgcaaaat gagactcaaa aagagattgc tggcattcag tcggcgactt    3480
cacgccagaa tacgaaagac caggtatatg cacaaaatga gatgcttgct atcaacaga     3540 aggagtctac tgctcgcgtt gcgtctatta tggaaaacac caatctttcc aagcaacagc    3600
aggtttccga gattatgcgc caaatgctta ctcaagctca aacggctggt cagtatttta    3660
ccaatgacca aatcaaagaa atgactcgca aggttagtgc tgaggttgac ttagttcatc    3720
agcaaacgca gaatcagcgg tatggctctt ctcatattgg cgctactgca aaggatattt    3780
ctaatgtcgt cactgatgct gcttctggtg tggttgatat ttttcatggt attgataaag    3840
ctgttgccga tacttggaac aatttctgga aagacggtaa agctgatggt attggctcta    3900
atttgtctag gaaataaccg tcaggattga caccctccca attgtatgtt tcatgcctc    3960 caaatcttgg aggctttttt atggttcgtt cttattaccc ttctgaatgt cacgctgatt    4020
attttgactt tgagcgtatc gaggctctta aacctgctat tgaggcttgt ggcatttcta    4080
ctctttctca atccccaatg cttggcttcc ataagcagat ggataaccgc atcaagctct    4140
tggaagagat tctgtctttt cgtatgcagg gcgttgagtt cgataatggt gatatgtatg    4200
ttgacggcca taaggctgct tctgacgttc gtgatgagtt tgtatctgtt actgagaagt    4260
taatggatga attggcacaa tgctacaatg tgctccccca acttgatatt aataacacta    4320
tagaccaccg ccccgaaggg gacgaaaaat ggttttaga gaacgagaag acggttacgc     4380
agttttgccg caagctggct gctgaacgcc ctcttaagga tattcgcgat gagtataatt    4440
accccaaaaa gaaaggtatt aaggatgagt gttcaagatt gctggaggcc tccactatga    4500
aatcgcgtag aggctttgct attcagcgtt tgatgaatgc aatgcgacag gctcatgctg    4560
atggttggtt tatcgttttt gacactctca cgttggctga cgaccgatta gaggcgtttt    4620
atgataatcc caatgctttg cgtgactatt ttcgtgtatat tggtcgtatg gttcttgctg    4680
ccgagggtcg caaggctaat gattcacacg ccgactgcta tcagtatttt tgtgtgcctg    4740
agtatggtac agctaatggc cgtcttcatt tccatgcggt gcactttatg cggacacttc    4800
ctacaggtag cgttgaccct aattttggtc gtcgggtacg caatcgccgc cagttaaata    4860
gcttgcaaaa tacgtggcct tatggttaca gtatgcccat cgcagttcgc tacacgcagg    4920
acgctttttc acgttctggt tggttgtggc ctgttgatgc taaaggtgag ccgcttaaag    4980
ctaccagtta tatggctgtt ggtttctatg tggctaaata cgttaacaaa aagtcagata    5040
```

```
tggaccttgc tgctaaaggt ctaggagcta aagaatggaa caactcacta aaaaccaagc      5100
tgtcgctact tcccaagaag ctgttcagaa tcagaatgag ccgcaacttc gggatgaaaa      5160
tgctcacaat gacaaatctg tccacggagt gcttaatcca acttaccaag ctgggttacg      5220
acgcgacgcc gttcaaccag atattgaagc agaacgcaaa aagagagatg agattgaggc      5280
tgggaaaagt tactgtagcc gacgttttgg cggcgcaacc tgtgacgaca aatctgctca      5340
aatttatgcg cgcttcgata aaaatgattg gcgtatccaa cctgca                    5386

<210> SEQ ID NO 6
<211> LENGTH: 10
<212> TYPE: DNA
<213> ORGANISM: phi X virus

<400> SEQUENCE: 6
acgttgcagc                                                               10
```